US006468753B1

(12) United States Patent
Smith et al.

(10) Patent No.: US 6,468,753 B1
(45) Date of Patent: Oct. 22, 2002

(54) ANTHRAQUINONE AND ITS DERIVATIVES

(75) Inventors: Paul James Smith, Vale of Glamorgan; Laurence Hylton Patterson, Anstey, both of (GB)

(73) Assignee: Biostatus Limited, Leicestershire (GB)

( * ) Notice: Subject to any disclaimer, the term of this patent is extended or adjusted under 35 U.S.C. 154(b) by 0 days.

(21) Appl. No.: 09/719,863

(22) PCT Filed: Jun. 15, 1999

(86) PCT No.: PCT/GB99/01904

§ 371 (c)(1),
(2), (4) Date: Feb. 20, 2001

(87) PCT Pub. No.: WO99/65992

PCT Pub. Date: Dec. 23, 1999

(30) Foreign Application Priority Data

Jun. 18, 1998 (GB) ............................................. 9813062

(51) Int. Cl.$^7$ .............................. C12Q 1/68; C09B 1/16
(52) U.S. Cl. ................................ 435/6; 435/4; 514/644; 552/236; 552/237; 552/240
(58) Field of Search .......................... 514/644; 552/236, 552/237, 240; 435/4, 6

(56) References Cited

U.S. PATENT DOCUMENTS

| 4,410,524 A | 10/1983 | Murdock | |
|---|---|---|---|
| 5,132,327 A | * 7/1992 | Patterson | ..................... 514/644 |

FOREIGN PATENT DOCUMENTS

| GB | 2 237 283 A | 5/1991 |
|---|---|---|
| WO | WO9105824 | 5/1991 |

OTHER PUBLICATIONS

Smith et al.("Flow Cytometric Analysis and Confocal Imaging of Anticancer Alkylaminoanthraquinones and their N–Oxides in Intact Human Cells Using 647–nm Krypton Laser Excitation", Cytometry, 27, 43–53, 1997).*

Paul J. Smith et al., "Flow Cytometric Analysis and Confocal Imaging of Anticancer Alkylaminoanthraquinones and Their N–Oxides in Intact Human Cells Using 647–nm Krypton Laser Excitation," Cytometry, vol. 27, No. 1, 1997, pp. 43–53.

Paul J. Smith et al., "DNA topoisomerase II–dependent cytotoxicity of alkylaminoanthraquinones and their N–oxides," Cancer Chemotherapy and Pharmacology, vol. 39, No. 5, 1997, pp. 455–461.

Laurence H. Patterson, "Rationale for the use of aliphatic N–oxides of cytotoxic anthraquinones as prodrug DNA binding agents: a new class of bioreductive agent," Cancer and Metastasis Reviews, vol. 12, 1993, pp. 119–134.

WR Wilson et al., "Tertiary amine N–oxides as bioreductive drugs: DACA N–oxide, nitracrine N–oxide and AQ4N," British Journal of Cancer, vol. 74, 1996, pp. 43–47.

Laurence H. Patterson et al., "Aliphatic Amine N–oxides of DNA Binding Agents as Bioreductive Drugs," Oncology Research, v. 6, 1994, pp. 533–538.

SR McKeown et al., "AQ4N: an Alkylaminoanthraquinone N–oxide Showing Bioreductive Potential and Positive Interaction with Radiation in vivo," British Journal Cancer, 72, 1995, pp. 76–81.

SR McKeown et al., "Evidence for a Therapeutic Gain when AQ4N or Tirapazamine is Combined with Radiation," British Journal of Cancer, 74, 1996, pp. S39–S42.

MV Hejmadi et al., "DNA Damage Following Combination of Radiation with the Bioreductive Drug AQ4N: Possible Selective Toxicity to Oxic and Hypoxic Tumour Cells," British Journal of Cancer, 73, 1996, pp. 499–505.

* cited by examiner

Primary Examiner—Jeffrey Fredman
(74) Attorney, Agent, or Firm—Young & Thompson

(57) ABSTRACT

There is disclosed a compound of formula (I) wherein each of $X_1$ and $X_2$ are independently NH—A—NR$^1$R$^2$, and wherein A is A $C_{2-8}$ alkylene group and $R^1$ and $R^2$ are independently selected from hydrogen, $C_{1-4}$ alkyl, $C_{2-4}$ hydroxy-alkyl and $C_{2-4}$ aminoalkyl, or $R^1$ and $R^2$ together form a $C_{2-6}$ alkylene group which with the nitrogen atom to which $R^1$ and $R^2$ are attached forms a heterocyclic ring, or an N-oxide derivative thereof, and wherein the compound (I) or its N-oxide derivative is optionally in the form of an acid salt derived from an organic or inorganic acid. Also disclosed is a method of its production and its uses, including its use in analyzing a cell or biological material and detecting the emitted fluorescence signal.

17 Claims, 19 Drawing Sheets

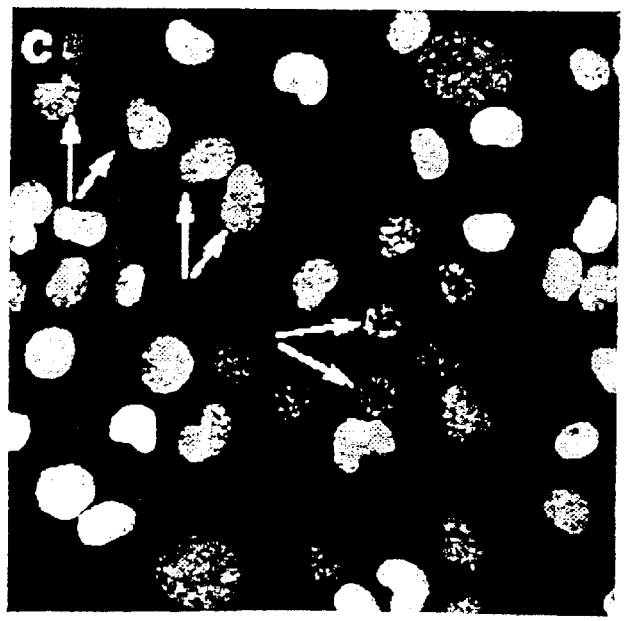
*Fig. 3c*
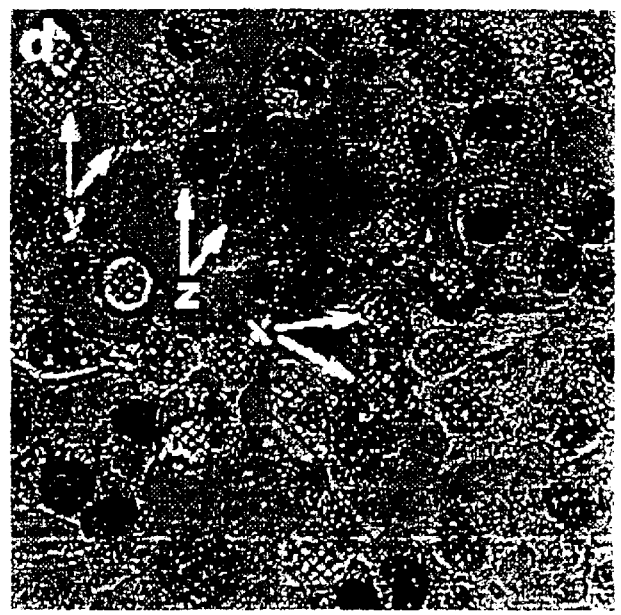
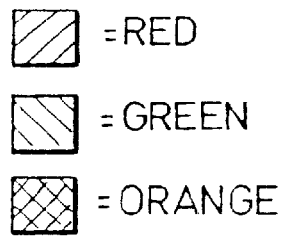 = RED
= GREEN
= ORANGE
*Fig. 3d*

☒ = RED
☒ = GREEN

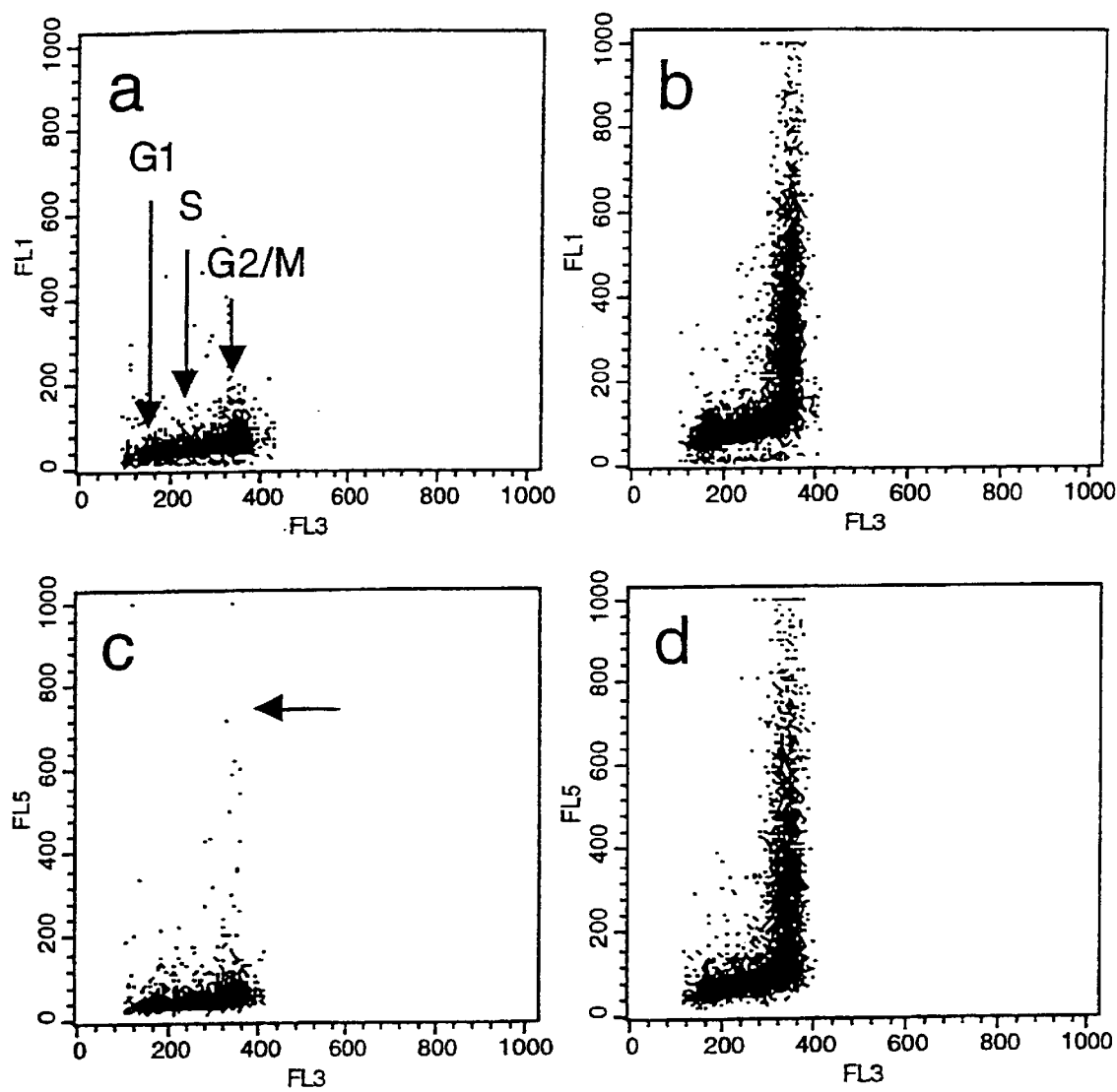
*Fig. 9a-d*

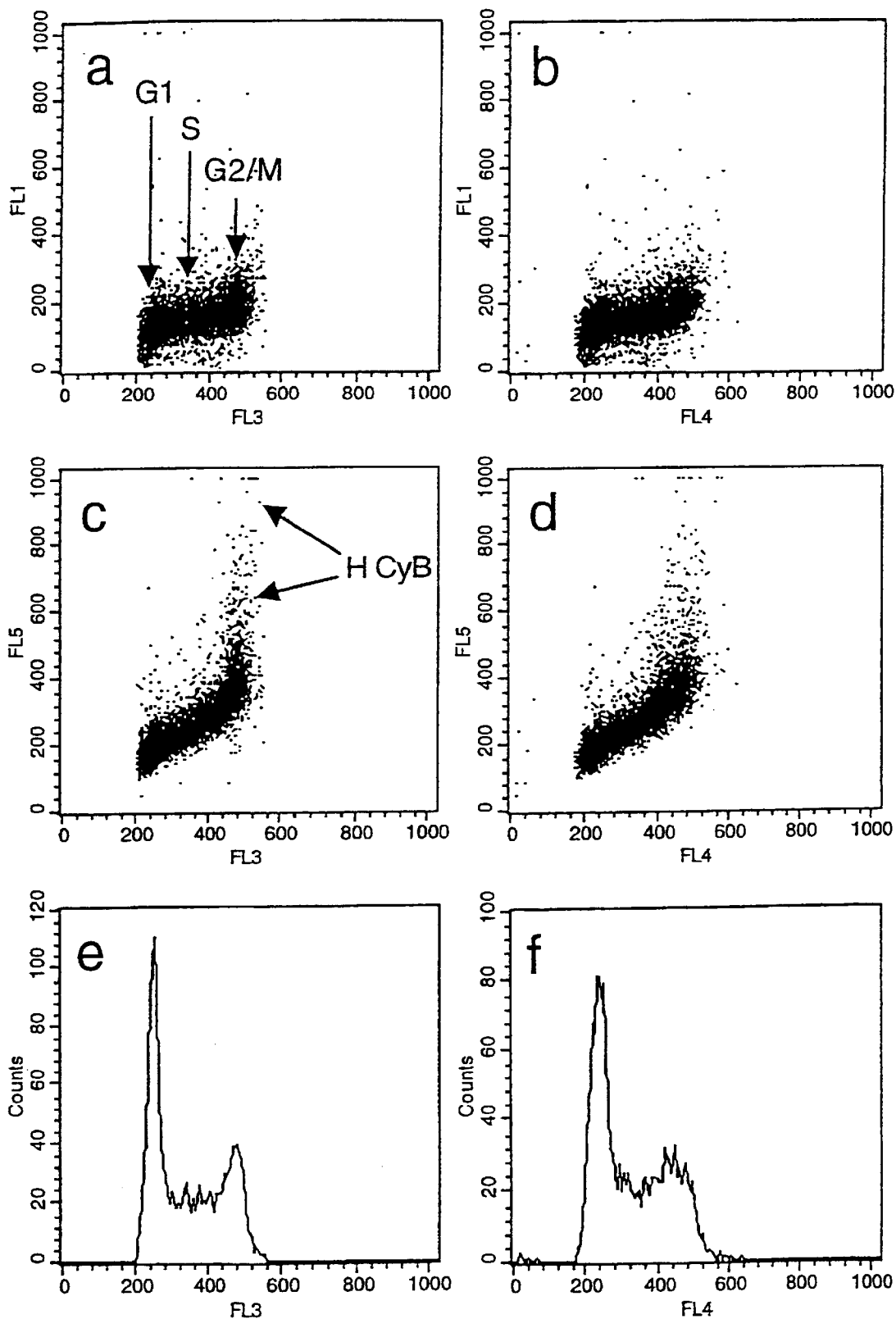
Fig. 10a-f

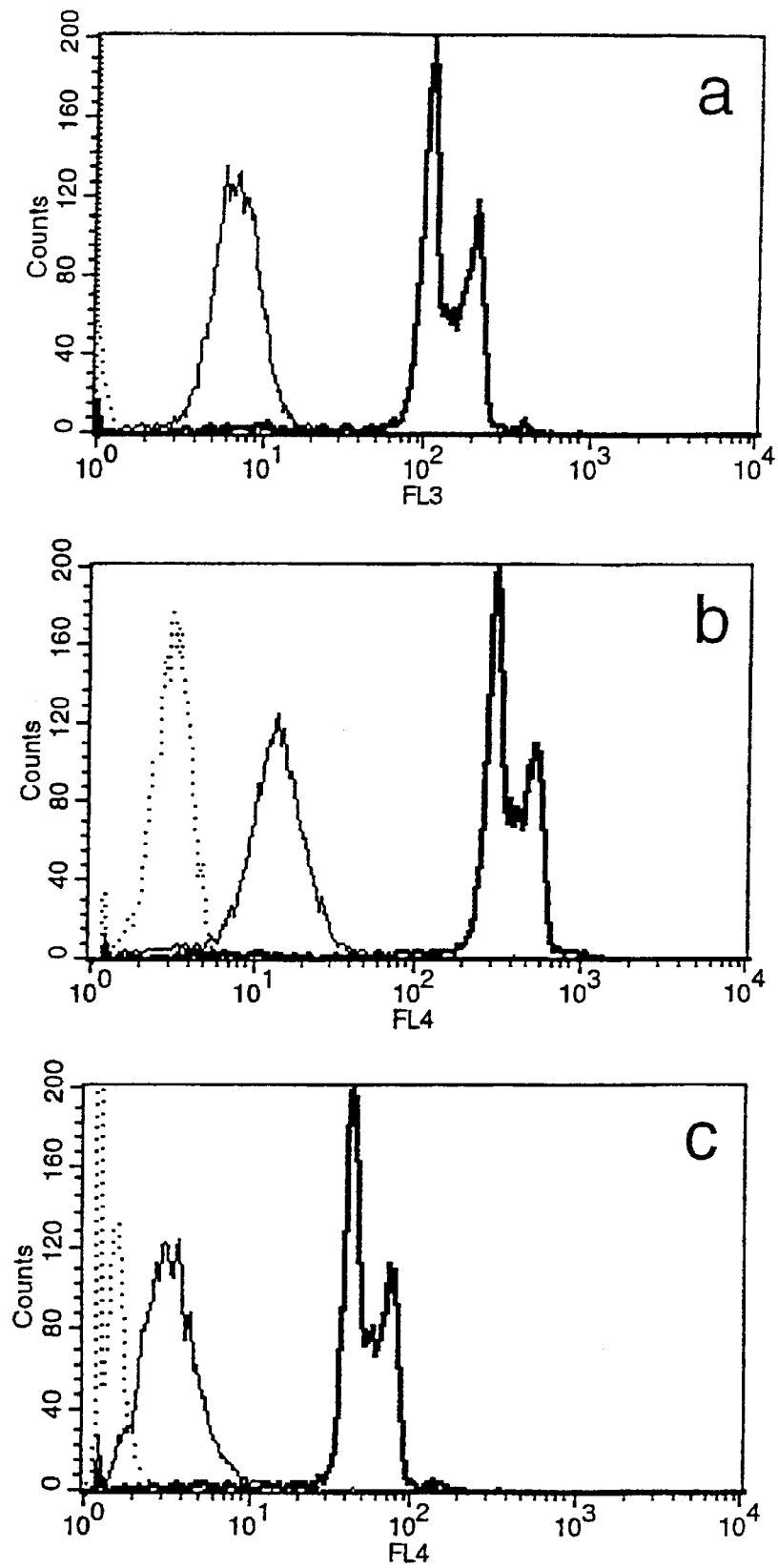
Fig. 11a-c

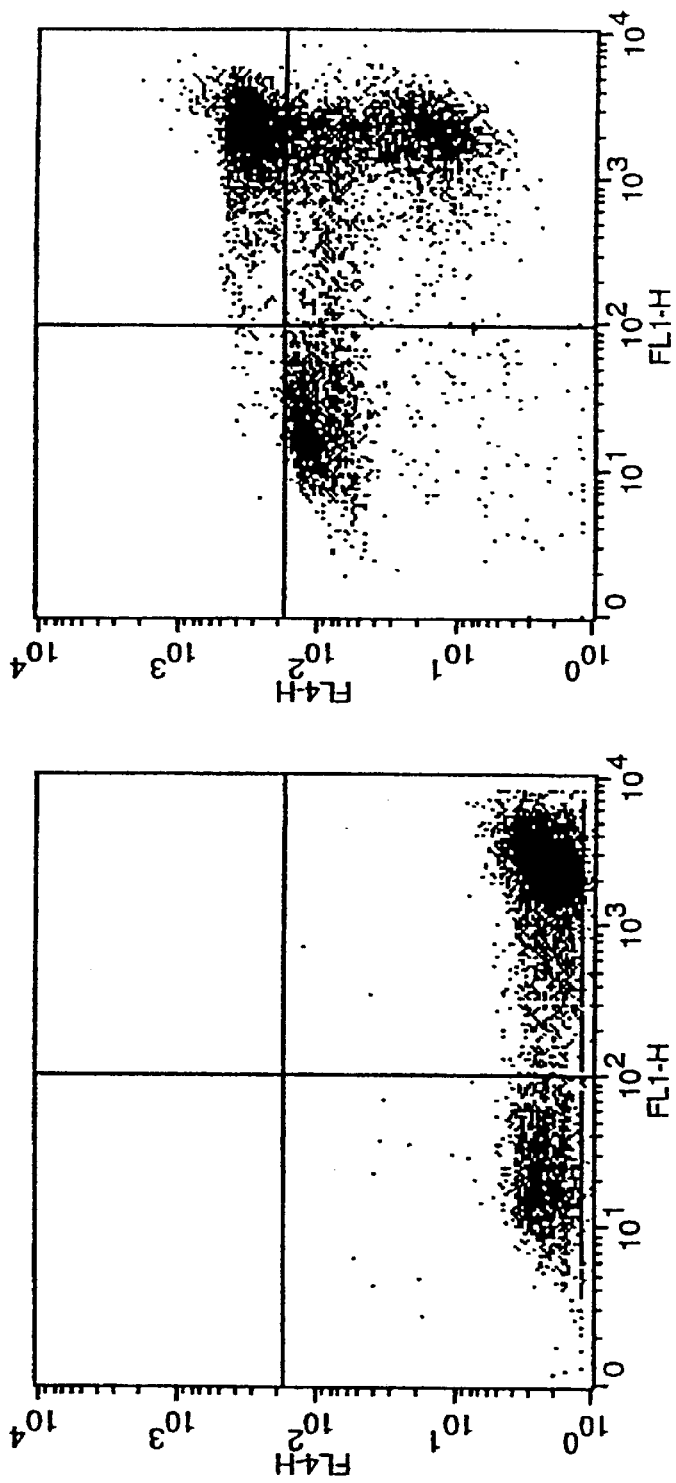

ANTHRAQUINONE AND ITS DERIVATIVES

This invention relates to an anthraquinone and its derivatives, in particular, although not exclusively, including its applications in a range of fluorescence detection technologies.

There are a number of DNA-binding fluorochromes available which cover the UV and visible region of the spectrum. Recently, very bright DNA-intercalating cyanine fluorochromes, based upon modified dimers of thiazole orange, have become commercially available. These cyanine dyes do not share the cell permeant properties of other DNA specific UV-activated fluorochromes. Furthermore, the commonly used DNA-interactive fluorochromes have fluorescent signatures which overlap those of other fluorochromes, activated in the spectral range of visible light, which are used as molecular tags to probe aspects of cell biology or biological structures. Examples of currently known cyanine dyes are disclosed in U.S. Pat. No. 5410030 and U.S. Pat. No. 5436134.

The present invention seeks to develop cell permeant DNA-interactive agents which may provide a fluorescence signature extending in to the infra red region of the spectrum. Such an agent could, for example, be optimally excited by red-line emitting lasers in multi-laser/multi-fluorochrome applications for both fixed specimens and viable cells.

Thus, in accordance with a first aspect of the present invention, there is provided a compound of the following formula (I):

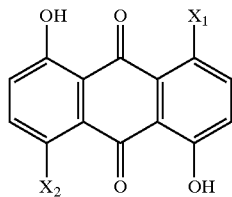

(I)

wherein each of $X_1$ and $X_2$ are independently NH—A—$NR^1R^2$, and wherein A is a $C_{2-8}$ alkylene group and $R^1$ and $R^2$ are independently selected from hydrogen, $C_{1-4}$ alkyl, $C_{2-4}$ hydroxyalkyl and $C_{2-4}$ aminoalkyl, or $R^1$ and $R^2$ together form a $C_{2-6}$ alkylene group which with the nitrogen atom to which $R^1$ and $R^2$ are attached forms a heterocyclic ring, or an N-oxide derivative thereof, and wherein the compound (I) or its N-oxide derivative is optionally in the form of an acid salt derived from an organic or inorganic acid.

The term "alkylene" here is used to mean an alkyl chain.

In a preferred embodiment, when $R^1$ and $R^2$ form a heterocyclic ring, the ring has 3 to 7 carbon atoms therein. Preferably, both $X_1$ and $X_2$ are both $NH(CH_2)_2NR^1R^2$. In particular, it is preferred that $R^1$ and $R^2$ are both $C_{1-4}$ alkyl groups, preferably methyl groups.

According to a second aspect of the present invention, there is provided a compound of the following formula (II):

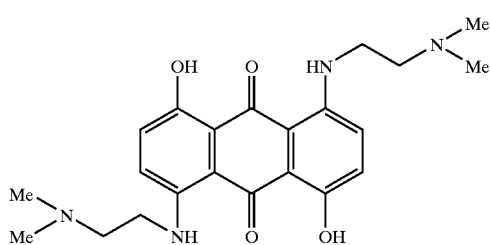

(II)

In one embodiment, compound (II) may be in the form of its N-oxide derivative.

The compound of the general formula (I) and, in particular the specific compound (II) may be used as, for example, a DNA dye and may be a pure synthetic compound which is soluble in biologically compatible solvents including water. Compound (II) has a high infinity for DNA (the DNA binding constant is approximately 10e7 M-1) and has the capacity to enter living cells rapidly.

The absorbance spectrum for compound (II) shows $Ex_{\lambda max}$ near 647 nm and produces a fluorescence spectrum extending from 665 nm out to beyond 780 nm wavelengths ($Em_{\lambda max}$ is about 677.5 nm).

According to a further aspect of the present invention, there is provided a method of preparing a compound of the following formula (I):

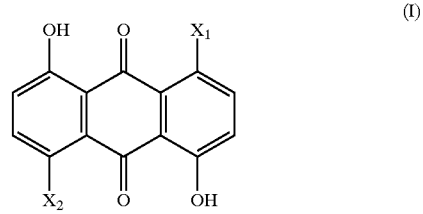

(I)

wherein each of $X_1$ and $X_2$ are independently NH—A—$NR^1R^2$, and wherein A is a $C_{2-8}$ alkylene group and $R^1$ and $R^2$ are independently selected from hydrogen, $C_{1-4}$ alkyl, $C_{2-4}$ hydroxyalkyl and $C_{2-4}$ aminoalkyl, or $R^1$ and $R^2$ together form a $C_{2-6}$ alkylene group which with the nitrogen atom to which $R^1$ and $R^2$ are attached forms a heterocyclic ring, or an N-oxide derivative thereof, and wherein the compound (I) or its N-oxide derivative is optionally in the form of an acid salt derived from an organic or inorganic acid, the method comprising the step of reacting a compound of the following formula (III)

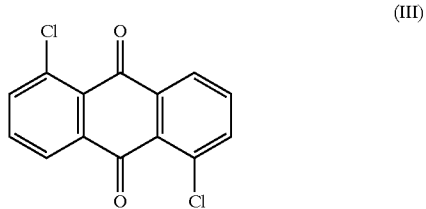

(III)

with $NH_2$—A—$NR^1R^2$, wherein A, $R^1$ and $R^2$ are as defined above.

The method preferably further comprises the step of treating the resultant compound with an acid, preferably concentrated sulphuric acid. In addition, in a preferred embodiment, the method may further comprise subsequent treatment with sodium chlorate and/or sodium hydrogen sulphite.

Modelling has demonstrated that the compounds of the present invention can form stable, intercalated complexes with DNA. Thus, according to a further aspect of the present invention, there is provided a fluorescent complex comprising a nucleic acid and a compound of the following formula (I):

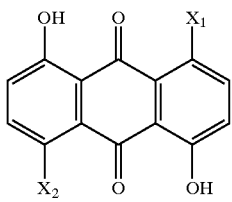

wherein each of $X_1$ and $X_2$ are independently NH—A—$NR^1R^2$, and wherein A is a $C_{2-8}$ alkylene group and $R^1$ and $R^2$ are independently selected from hydrogen, $C_{1-4}$ alkyl, $C_{2-4}$ hydroxyalkyl and $C_{2-4}$ aminoalkyl, or $R^1$ and $R^2$ together form a $C_{2-6}$ alkylene group which with the nitrogen atom to which $R^1$ and $R^2$ are attached forms a heterocyclic ring, or an N-oxide derivative thereof, and wherein the compound (I) or its N-oxide derivative is optionally in the form of an acid salt derived from an organic or inorganic acid.

The nucleic acid is preferably DNA. It has been found that the DNA may be present in a living cell. The compounds of the present invention may stain fixed human chromosomes. As the DNA:Compound molar ratio increases there is a bathochromic shift in the compound plus DNA solution spectrum. At high DNA:Compound ratios, attainable within living cells, the spectral shift contributes to an already significant separation of the compound-DNA emission spectrum from that of an example of a red-fluorescing compound Cy 5.

According to a further aspect of the present invention, there is provided a method of analysing a cell or biological material containing one or more nucleic acids, comprising the steps of:

a) preparing a biologically compatible solution containing a compound of the formula (I):

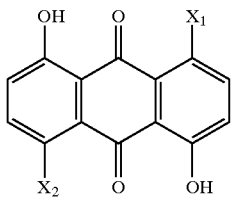

wherein each of $X_1$ and $X_2$ are independently NH—A—$NR^1R^2$, and wherein A is a $C_{2-8}$ alkylene group and $R^1$ and $R^2$ are independently selected from hydrogen, $C_{1-4}$ alkyl, $C_{2-4}$ hydroxyalkyl and $C_{2-4}$ aminoalkyl, or $R^1$ and $R^1$ together form $C_{2-6}$ alkylene group which with the nitrogen atom to which $R^1$ and $R^2$ are attached forms a heterocyclic ring, or an N-oxide derivative thereof, and wherein the compound (I) or its N-oxide derivative is optionally in the form of an acid salt derived from an organic or inorganic acid;

b) treating the cell or biological material with the biologically compatible solution;
c) exciting the compound (I) in the treated cell or biological material with a light source; and
d) detecting the emitted fluorescence signal.

The compound of formula (I) may be present in its free state or be complexed to other molecule(s), for example either by covalent or non-covalent attachment.

The light source preferably provides wavelength(s) in the spectral region of the wavelength(s) of maximum absorption of compound (I).

It has been found that the fluorescence signature of the compounds of the present invention extends to the infra red region of the spectrum. The compound of the present invention may be present in the cell or biological material in combination with one or more other fluorochromes or light-emitting compounds. The other fluorochromes may emit in the UV or visible region of the spectrum. Thus, the compounds of the present invention lend themselves to multi-parameter analysis with other fluorochromes with spectra which overlap with those of the commonly used visible-region DNA probes.

The one or more other compounds may be used, for example, to detect Annexin V and is preferably used in combination with the N-oxide derivative of compound (I). Flow cytometric analysis, for example with the instrument in dual laser mode, may be used. The invention thus may provide a way of discriminating intact viable cells from those undergoing the various stages of cell death.

Thus, the compounds of the present invention provide far red/infra red fluorescent permeant DNA dyes suitable for cellular DNA analysis where intact cells may be required, for example the detection of molecules either on the cell surface (e.g. a receptor molecule or marker for differentiation) or within cells (e.g. cytosolic enzymes) by methods which require the maintenance of membrane integrity to prevent perturbation or loss of such molecules.

As mentioned above, in this method, the compounds of the present invention may stain nucleic acids in fixed human chromosomes, fixed cells and fixed biological materials, and in procedures which modify the permeability of living cell membranes.

According to a further aspect of the present invention, there is provided the use of compound (I) in a biological assay. Compound (I) may be present either in its free state or complexed to other molecules by either covalent or non-covalent attachment in the biological assay. Compound (I) may be present as an N-oxide derivative thereof. The biological assay is preferably a rapid and/or large capacity handling procedure. The use of the compounds of the present invention, as indicated by compound (I), as a discriminating or orientating parameter for cell nuclei has been demonstrated for both flow cytometry and confocal laser scanning microscopy.

In accordance with a further aspect of the present invention, there is provided the use of compound (I) in cytometry. Compound (I) is optionally present as an N-oxide derivative thereof. The cytometry process may be, for example, single beam or multi-beam flow cytometry.

By way of example, single beam (488 nm) flow cytometry has been used to demonstrate the utility of compound (I)-nuclear DNA fluorescence (preferably compound (II)-nuclear DNA fluorescence) as a discriminating parameter for human blood and lymphoma cells, in combination with fluorochrome-labelled antibodies for the detection of surface antigens and subpopulation recognition. Compound (I) fluorescence was found to reflect cellular DNA content as evidenced by cell cycle DNA distribution profiles for exponentially proliferating cell populations showing a steady-state or asynchronous distribution of cells with respect to cell cycle age, or for perturbed cell populations in which, for example, drug action has caused the delay or arrest of cells at a given point in the cell cycle. In one embodiment, dual beam (488 nm/633 nm) flow cytometry shows the selective excitation of compound (I), preferably compound (II), and fluorescein in intact cells. In addition, in one embodiment, the application of compound (I), preferably compound (II), in triple beam flow cytometry (multiline UV/488 nm/633 nm) has been demonstrated in applications involving delayed signal discrimination where beam separation allows for the discrimination of the excitation beam associated with a fluorescence emission signal by reference to the delay in signal arrival at a detector.

According to a further aspect of the present invention, there is provided the use of compound (I) in microscopy. Compound (I) may be present as its N-oxide derivative. Preferably the microscopy is confocal laser scanning microscopy (CLSM). By way of example, CLSM employing either 647 nm or 568 nm wavelength excitation of intracellular compound (I), preferably intracellular compound (II), shows fluorescence specifically located in the nucleus revealing nuclear architecture within living or fixed human cells.

According to a further aspect of the present invention, there is provided the use of compound (I) as a nuclear staining agent. Compound (I) may be present as its N-oxide derivative.

According to a further aspect of the present invention, there is provided the use of compound (I) as an imaging agent. Compound (I) may be present as its N-oxide derivative.

In one embodiment, compound (I) can be used as an imaging agent in multi-photon excitation imaging.

Dual wavelength imaging, using compound (I) to reveal nuclear form, may be used to demonstrate the heterogeneity in esterase-dependent fluorescein loading of whole cells and in the assessment of mitochondrial function by rhodamine 123 labelling. In such imaging applications, compound (I) shows no evidence of photo bleaching and was persistent.

Thus, the compounds of the present invention can be considered as a fluorochrome for application as an agent in the use, calibration, standardization, and configuration of fluorescence-based systems. The preferred compound of the present invention is compound (II)-deep red fluorescing bisalkylaminoanthraquinone (DRAQ5).

It has been found that the high penetration of red line laser beams into tissues and the permeant properties of the compounds of the present invention provide a combination which allows three dimensional orientation and location of nuclei within living tissues. In addition, the availability of low cost HeNe lasers or other red light-emitting devices with enhanced power enables the compounds of the present invention to find applications in detection systems where their fluorescence signature can be used as a discriminating parameter.

Whilst the invention has been described above, it extends to any inventive combination of the features set out above or in the following description.

The invention will now be described, by way of example, with reference to the accompanying drawings and examples, and in which:

FIGS. 1a to c show spectral characteristics of DRAQ5;

FIGS. 2a to f show spectral characteristics of DRAQ5 associated DNA fluorescence detected by CLSM;

FIG. 2g shows the multi-photon imaging of DRAQ5 stained cell nuclei;

FIG. 2h to k shows a comparison of viable cells stained by DRAQ5 or its N-oxide derivative (DRAQ5N);

FIGS. 3a to d show differential excitation of fluorescein and DRAQ5 in viable A375 cells analysed by CLSM;

FIGS. 4a to c show the differential excitation of rhodamine 123 and DRAQ5 in viable A375 cells analysed by confocal laser scanning microscopy;

FIG. 5 shows flow cytometric analyses of DRAQ5 accumulation, for a one hour exposure period, in viable HL60 cells;

FIGS. 6a to d show dual beam flow cytometric analysis for the detection of DRAQ5-associated fluorescence in fluorescein-labelled viable HL60 cells;

FIGS. 7a to d show single beam flow cytometric analysis of DRAQ5 fluorescence versus antibody fluorescence for cultured and blood-derived human cells;

FIG. 9 shows dual beam flow cytometric analysis of the cell cycle specific expression of cyclin B1;

Figure 1A:
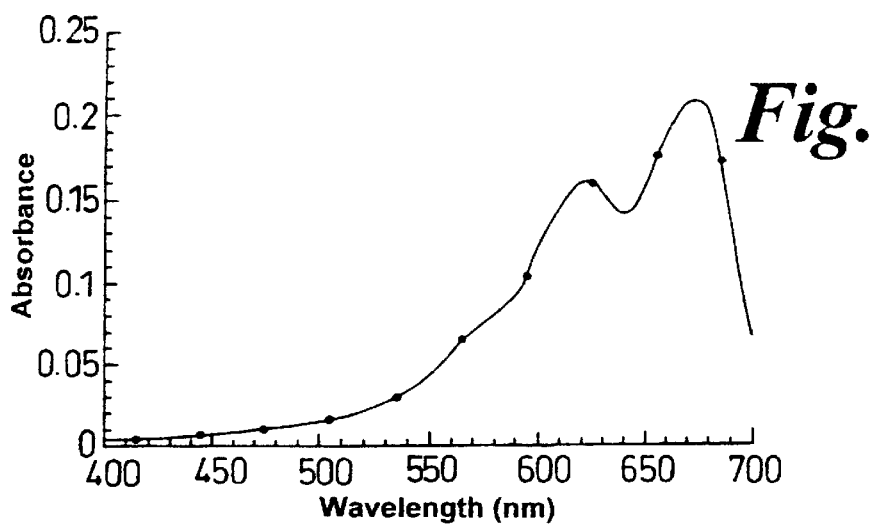

FIGS. 10a to f show triple beam flow cytometric analysis of DRAQ5-stained fixed and RNaseA digested asynchronous SUD4 lymphoma cells;

FIGS. 11a to c show the flow cytometric analysis of cellular DNA content of intact SUD4 lymphoma cells using 488 nm, 633 nm or multi-line UV excitation;

FIGS. 12a–d illustrate examples of cellular accumulation, using a human B cell lymphoma cell line, using combinations of reagent treatments; and FIGS. 13a–d illustrate examples showing the same combination of reagents for VP-16 treated cultures.

EXAMPLE 1

Synthesis of DRAQ5

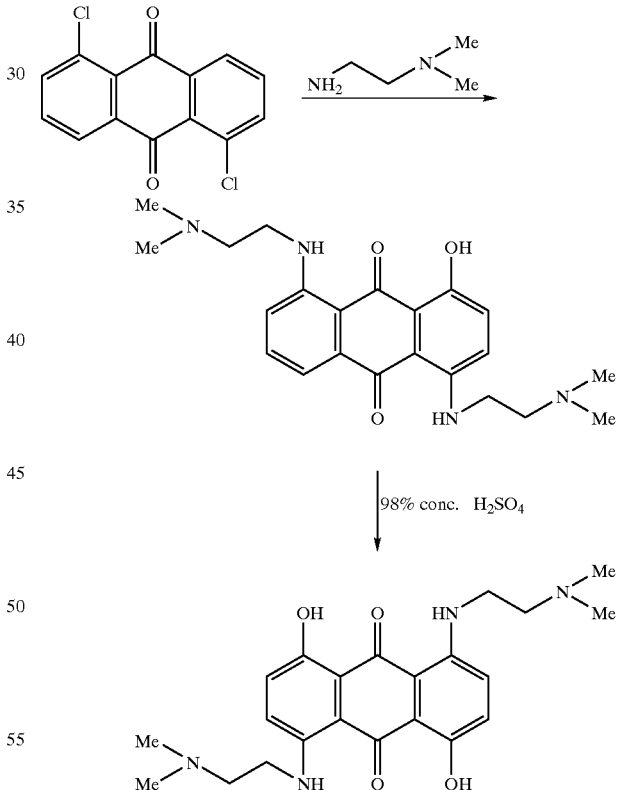

Procedure:

1,5-dichloroanthroquinone (15 g, 54 mmoles) was dissolved in N,N-dimethylethylenediamine (47.6 g, 540 mmoles) are refluxed for 18 h. The reaction was monitored by TLC (9:1 $CH_2Cl_2$/MeOH). The mixture was cooled to room temperature and diluted with water to precipitate the titled compound. The filtered solid was recrystallised from methanol to afford (A) (15.89, 89%) as a crystalline solid. $R_f$ (9:1 $CH_2Cl_2$/MeOH) :0.60.

¹H NMR (CDCl₃): δ 9.8 (t,2H), 7.6 (m, 4H), 6.9 (m, 2H) 3.4 (q, 4H), 2.7 (t, 4H), 2.4 (5, 12H). Mass spectrum, m/z 381 (m⁺+1).

The anthracene-9,10-dione derivative (A) (6 g, 15. 8 mmoles was dissolved in 65 g of concentrated $H_2SO_4$ and cooled to −10° C. Anhydrous sodium chlorate (6.5 g, 61.6 mmoles) was added in portions over 1.5 h and the mixture then stirred for 3 h at room temperature. The blue solution was added slowly to a cold sodium hydrogen sulfite solution (1%, 1000ml). The mixture was neutralised to pH7 with 5M NaOH. The titled compound (B) was extracted from the aqueous phrase with $CH_2Cl_2$ and concentrated under vacuo. Column chromatography ($SiO_2$, 9:1 $CH_2Cl_2$/MeOH) gave (B) (1.2 g, 20%).

EXAMPLE 2

Synthesis of DRAQ5N [1,5-Bis-((2-dimethylamino-N-oxide)ethyl)amino)-4,8-dihydroxyanthracene-9,10-dione]

The title compound was prepared from example 1 (DRAQ5) as follows. DRAQ5 (0.1 g, 24 mmol) was added to meta-chloroperoxybenzoic acid (80% purity, 0.186 g, 0.96 mmol) in dry dichloromethane and left at −20° C. overnight. The crude product was subjected to silica column chromatography using 9:1:0.1 dichloromethane:methanol:ammonia (0.88 sp.gravity) as an eluting solvent. The title compound was isolated as a blue powder. Melting Point 221° C. 1H NMR (CD3OD) d (delta) 7.39 (d, 2H), 7.2 (d, 2H), 4.0 (t, 4H), 3.65 (t, 4H), 3.30 (S, 12H) 13C NMR (CD3OD): d (delta) 189, 156.5, 147, 130, 122.5, 116, 69.5, 59.5, 38.5. Mass spectrum m/z 445(M++1).

EXAMPLE 3

Spectral Analysis of DRAQ5

Absorbance spectra were obtained using a Perkin-Elmer Lambda 16 UV spectrometer and a 10 μM solution of agent dissolved in dichloromethane and measured in a 1 cm path length quartz-silica cuvette. Fluorescence spectra for a 0.8 ml solution of 20 μM DRAQ5 in a 1 cm path length semi-micro quartz silica cuvette were determined by exciting at 647 nm wavelength or monitoring emission at 670 nm wavelength. Fluorescence measurements were made on a Perkin Elmer LS50 spectrofluorometer with slit widths set at 10 nm. The spectrofluorometer was equipped with a red-sensitive photomultiplier tube (PMT; type R928; Hamamatsu Photonics KK, Japan). Data were accumulated for four scans for each condition and exported into a spreadsheet program to correct values for the buffer control and to determine emission maxima. DNA-DRAQ5 fluorescence was measured by the addition of microlitre volumes of concentrated calf thymus DNA solutions to the cuvette with mixing. Both agent and DNA were prepared in DNA binding buffer (0.05 M sodium phosphate, pH 6.2, 0.05 M NaCl, 0.001 M EDTA; 3). The spectra shown were corrected for the buffer background and not for the spectral sensitivity of the PMT. Rhodamine 123 spectra were generated in DNA binding buffer using either 488/5 nm excitation or monitoring emission at 530/5 nm. Previously published excitation and emission spectra, were obtained from original source files and normalised for peak intensity.

Spectral Characteristics and Interaction of DRAQ5 with DNA

Figure 1B:
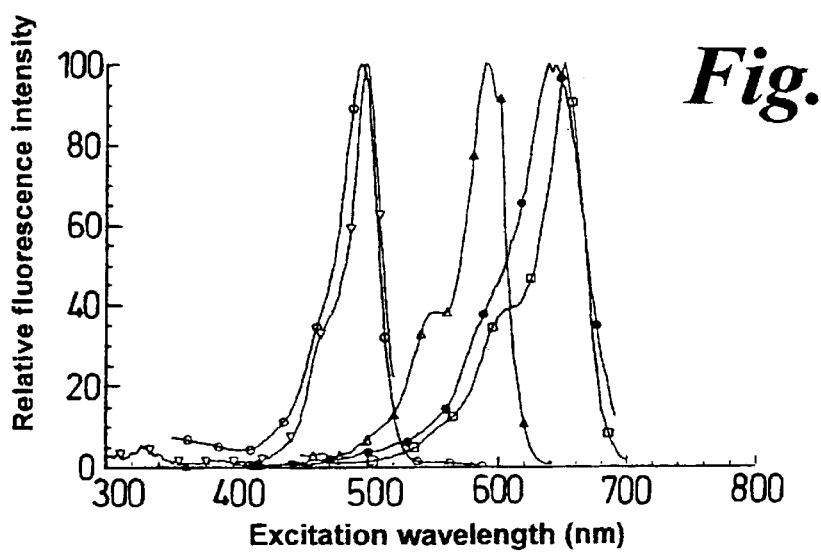
Figure 1C:
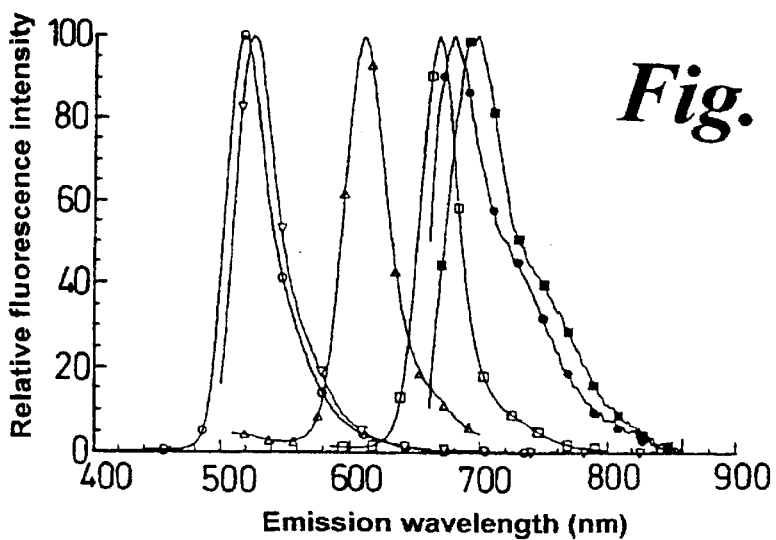

FIGS. 1a–c show spectral characteristics of DRAQ5. FIG. 1a: Visible absorbance spectrum for DRAQ5 (10 μM in dichloromethane).

FIG. 1b, Comparison of excitation spectra for specified emission wavelengths for: FITC (○, 620 nm emission), rhodamine 123 (▽, 0.5 μg/ml, 530 nm emission), Texas Red (Δ; 660 nm emission), Cy 5.18 (□, 715 nm emission), DRAQ5 (●, 670 nm emission).

FIG. 1c: Comparative emission spectra for specified excitation wavelengths for FITC (○, 425 nm excitation), rhodamine 123 (▽, 0.5 μg/ml, 488 nm excitation), Texas Red (Δ, 500 nm excitation), Cy 5.18 (□, 570 nm excitation), 20 μM DRAQ5 (●, 647 nm excitation), and 20 μM DRAQ5 plus 1280 μM DNA (●, 647 nm excitation).

FIG. 1a shows the visible absorbance spectrum for DRAQ5 in phosphate buffer at pH 7.4. The spectrum gave maxima at 622 and 676 nm, in addition to maxima (data not shown) at 240 nm and 314 nm. The extinction coefficient at 676 nm wavelength was determined as 20949 $cm^{-1}mol^{-1}$. The fluorescence characteristics of DRAQ5 were studied to permit the interpretation of fluorometric data generated by flow cytometry and confocal imaging. An excitation spectrum was generated for the 460–660 nm range for emission at 680 nm wavelength and compared with one optimised for rhodamine 123 and those for other fluorochromes. FIG. 1b shows that DRAQ5 excitation in the 630–650 nm region is essentially similar to the excitation spectrum of the cyanine dye Cy 5.18 ($Ex_{\lambda max}$ 649 nm) but distinct from that of Texas Red ($Ex_{\lambda max}$ 596 nm), rhodamine 123 ($Ex_{\lambda max}$ 511 nm) and fluorescein isothiocyanate (FITC; $Ex_{\lambda max}$ 490 nm). In all cases shown in FIG. 1, spectra have been normalised to the intensity values at either the $Ex_{\lambda max}$ or $Em_{\lambda max}$.

The emission spectrum of DRAQ5 alone (FIG. 1c) showed that for 647 nm excitation there is significant emission is extending from 665 nm out to beyond 780 nm wavelengths with an $Em_{\lambda max}$ of 677.5 nm. The emission spectrum is significantly red-shifted compared with that of Cy 5.18. DRAQ5 appears to shows residual excitability at much lower wavelengths although fluorescence intensity for 514 nm wavelength excitation was reduced for DRAQ5 when compared with the values for excitation at 647 nm, in keeping with the characteristics of the excitation spectrum (data not shown).

Molecular modelling suggests that DRAQ5 is capable of binding to DNA through intercalation, the side chains on opposing sides of the aromatic ring structure each having the potential to stabilise the molecule on DNA.

Fluorometric experiments indicate that DNA affects DRAQ5 fluorescence in a complex manner with increasing DNA:DRAQ5 ratios associated with a red shift of $Em_{\lambda max}$ to 697 nm at a molar DNA:DRAQ5 ratio of 64. This shift upon DNA interaction is shown in FIG. 1c. At high DNA:DRAQ5 ratios, equivalent to those encountered in vital cell staining, loss of DRAQ5 signal due to any dye-dye quenching effects appears to be minimal. The red shift of $Em_{max}$ and the considerable low infra red/infra red signal at wavelengths beyond 730 nm distinguishes this probe from Cy 5.18 despite similar excitation characteristics.

EXAMPLE 4

Imaging and Microscopy Applications of DRAQ5 as a Novel Deer Red/Infra Red Fluorescent DNA-binding Probe Preferred aspects of the invention relate to the development of a cell permeant DNA-interactive dye, capable of acting as a discriminating or orienting marker for cellular DNA, with a fluorescence signature extending into the infra red region of the spectrum. The invention permits multi-laser, multi-fluorochrome and multi-photon excitation microscopy methods to be used with both fixed specimens and viable cells. Here we describe the spectral characteristics of DRAQ5 and demonstrate the potential applications of this DNA probe for multiparameter analysis of living and fixed cells using confocal laser scanning microscopy.

Cell Culture

The human melanoma cell line A375 was grown as asynchcronous cultures in Eagle's minimum essential medium supplemented with 10% foetal calf serum, 1 mM glutamine and antibiotics and incubated at 37° C. in an atmosphere of 5% $CO_2$ in air. For imaging experiments, cells were grown at a density of $5\times10^4$ cells/well as a monolayer on autoclaved glass coverslips in 6-well plates for 48 h prior to treatment. Attached viable cells were mounted in fresh PBS for microscopy. Where indicated, attached cells were fixed with 70% methanol at −20° C. for 10 min prior to rehydration and staining with ethidium bromide at 5 λg/ml for 10 min in the presence of 5 mg/ml RNase A.

Drug Preparation and Treatment

DRAQ5 was synthesised using the principles described and stored at +4° C. as an aqueous stock solution of 10 mM. DRAQ5 dilutions were prepared in phosphate buffered saline (PBS) and added directly to cultures. Fluorescein diacetate (FDA; Koch Light Laboratories) was prepared as a stock solution of 12 mM in acetone and stored at −20° C. Cells were treated with 0.2 $\mu$M FDA for 10 min at 37° C. either alone or after a 50 min exposure to DRAQ5. Likewise DRAQ5-treated cells were labelled with rhodamine 123 (laser grade; Kodak) at 2 $\mu$g/ml culture medium for 10 min, prior to analysis.

Confocal Laser Scanning Microscopy (CLSM) of Intact Cells

The system used was a Leica TCS 4D (LaserTechnik Gmbh, Germany) scanner coupled to a Leitz DM R microscope and operating with an Ominchrome argon/krypton laser. The laser provided emission lines at 488, 568 and 647 nm with variable power. Coverslip cultures were washed briefly in PBS, mounted in inverted positions on glass slides, the cover-slips being supported at the edges by a piping of petroleum jelly to prevent the cells from being compressed. The slides were examined immediately using ×100 or ×40 oil immersion objective lenses with mid-range pinhole and photomultiplier gain settings. Excitation/emission wavelengths for DRAQ5, fluorescein and rhodamine 123 were 647 nm/>665 nm, 488 nm/>515 nm and 488 nm/>590 nm respectively.

Gain settings were adjusted such that the most fluorescent drug-treated sample gave pixel intensities just below saturation. The black level/offset was adjusted to give effectively zero background (<4 for pixel value) after 16x is line noise filtration of images for untreated controls. Using this approach, the untreated controls showed minimal autofluorescence and gave no discernible image obviating the need for a background correction. Saved images were converted for analysis and merging using IP Lab Spectrum Image analysis software (Signal Analytics Corp. Vienna, Va., USA).

CLSM Analysis of DRAQ5 Fluorescence in Viable Cells

Figure 2A:
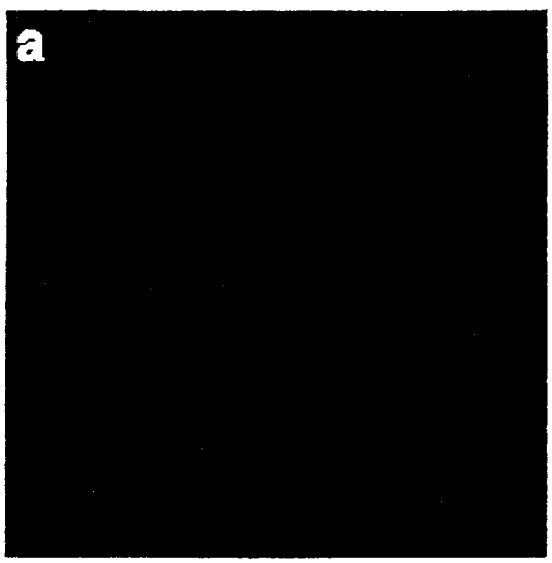
Figure 2B:
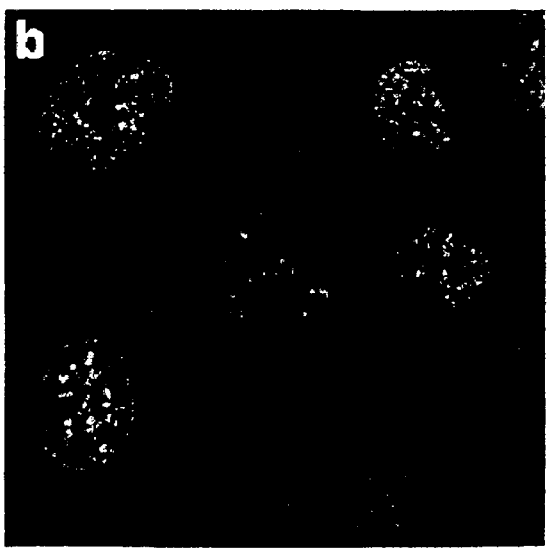
Figure 2C:
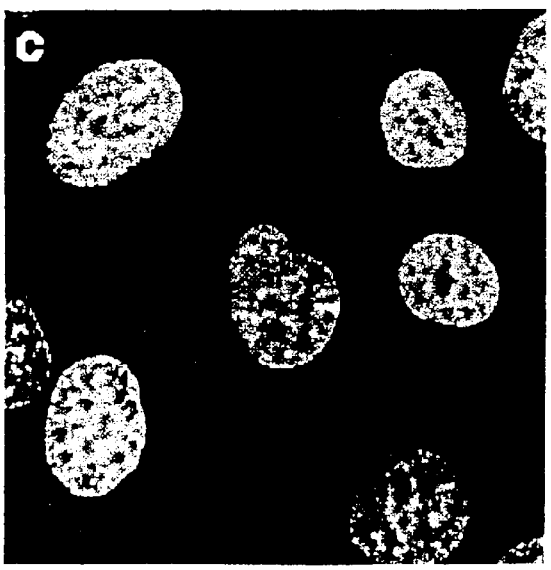
Figure 2D:
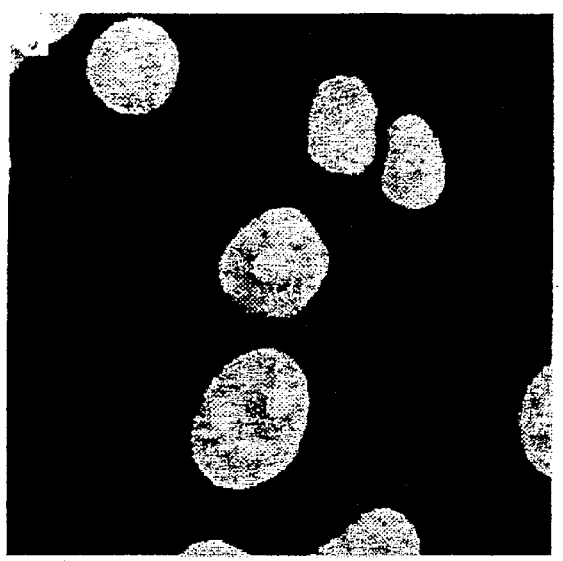
Figure 2E:
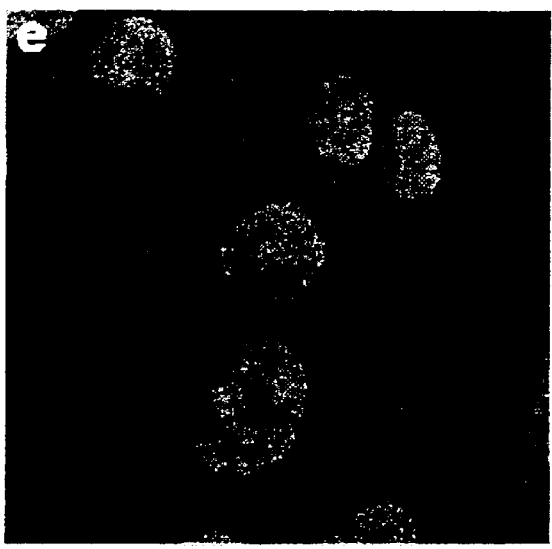
Figure 2F:
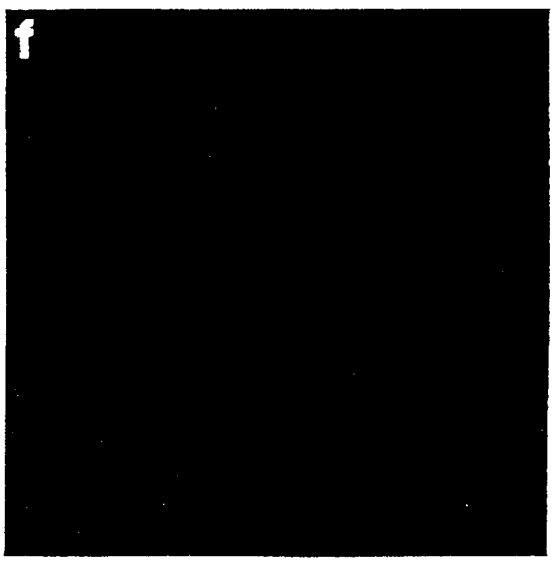
Figure 2G:
Figure 2H:
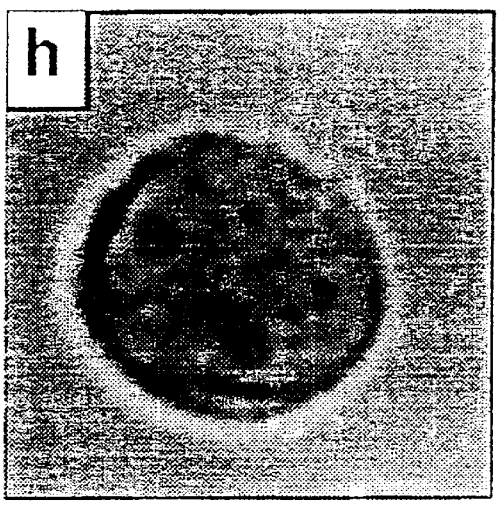
Figure 2I:
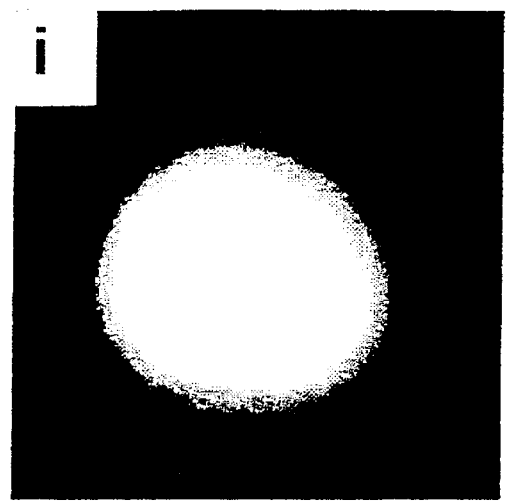
Figure 2J:
Figure 2K:
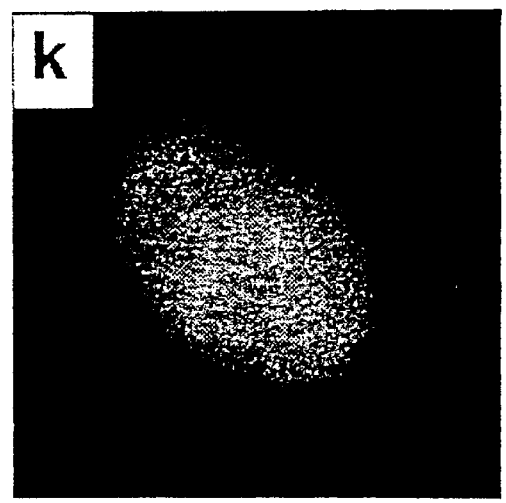

To gain some insight into the dependence of DRAQ5 fluorescence on the excitation wavelength and the spectral separation of its fluorescence signal from that of another DNA probe, we have compared cells stained with either DRAQ5 or ethidium bromide. The sensitivity range of the CLSM at either 488 nm or 568 nm excitation was optimised with respect to fluorescence of ethanol-fixed cells stained with ethidium bromide (FIGS. 2d–f), while imaging at 647 nm excitation was optimised on DRAQ5-treated viable cells (FIG. 2c). FIGS. 2a–f shows that at fluorochrome concentrations adequate for imaging nuclei and with appropriate emission filtration, 488 nm and 647 nm excitation conditions can be used to exclusively image either ethidium bromide or DRAQ5 staining respectively. DRAQ5 could also be used to image fixed cells with retention of much of the nuclear architecture observable in intact, viable cells (data not shown). Fluorescence activation has also been observed using multi-photon excitation of fixed cells stained with DRAQ5 (human B cell lymphoma cells; ethanol fixed; 20 $\mu$M DRAQ5; YLF mode-locked laser excitation at 15 mW using a modified MRC600 confocal imaging system; $Ex_\lambda$= 1047 nm; $Em_\lambda$=far red; FIG. 2g).

Using CLSM with 647 nm excitation (FIG. 2c) there was clear demonstration of nuclear-located fluorescence, quite different from other anthraquinone- and anthracycline-based agents screened which produced both nuclear and cytoplasmic signals. FIG. 2c shows that DRAQ5-treated viable cells display clear definition of nuclear architecture and the definition of the edges of nucleolar and nuclear membrane regions.

Thus, FIGS. 2a–f show spectral characteristics of DRAQ5-associated DNA fluorescence detected by CLSM: Panels a–c, excitation at 488, 568 and 647 nm wavelengths respectively for viable human A375 melanoma cells. Panels d–f, excitation at 488, 568 and 647 nm wavelengths respectively for ethanol-fixed cells stained with ethidium bromide. Images are 100×100 $\mu$m.

Multi-photon Imaging of DRAQ5

The principle of 2-photon excited fluorescence microscopy was first demonstrated by Webb and co-workers (Science, 248, 73–76 (1990); U.S. Pat. No. 5,034,613). In essence this involves the capture of two photons by an excitable molecule by arranging excitation conditions which favour such events. The excitation spectrum for a given fluorochrome for multi-photon events differs from the corresponding single photon excitation spectrum although the emission spectra are independent of the excitation mode. The key component of the excitation system, as applied to imaging, is a tuneable or fixed wavelength mode-locked laser, giving ultra-short pulses at high repetition rate. The multi-photon microscope typically incorporates a tuneable Ti-Sapphire laser emitting within the wavelength range 700–950 nm, with pulse widths of approximately 100 femtoseconds, and a repetition rate of 80 MHz. Fixed wavelength lasers can also be used such as a YLF mode-locked laser providing multi-photon excitation at 1047 nm. The peak intensity of such lasers is so high that dye excitation can occur by absorption of two or more photons in rapid succession. Importantly, multi-photon excitation avoids the need for short (e.g. UV) excitation wavelengths. Furthermore, since fluorescence excitation is localized to the region of the focal spot the multi-photon system can optically section a scanned object with restricted bleaching. Multi (dual) photon excitation of DRAQ5 has been achieved using YLF mode-locked laser and an example of a collected image showing nuclear-located fluorescence in fixed cells is shown in FIG. 2g. We have also observed multi-photon excitation of DRAQ5 in the nuclei of fixed cells using a Ti-Sapphire laser (pumped with 5W) emitting at 740 nm wavelength (consistent with the ability to UV excite DRAQ5-treated cell nuclei, as shown in FIG. 11). It is expected that the excitation spectrum for DRAQ5, consistent with the findings for other fluorochromes, differs from that determined by single-photon spectroscopy. The penetrance of infra red laser beams offers applications for multiphoton excitation of DRAQ5 in deep section/tissue scanning for nuclei location, quantification and morphology permitting accurate 3D reconstruction of complex cellular environments.

FIG. 2g shows the multi-photon imaging of DRAQ5 stained cell nuclei. Human B cell lymphoma cells were fixed with ethanol and stained with 20 μM DRAQ5. YLF mode-locked laser excitation at 15 mW ($Ex_\lambda$=1047 nm; $Em_\lambda$=far red) was used and images gained using 60×N.A. 1.4 oil objective, a zoom factor of 1.9 and a Kalman averaging of 37 frames.

CLSM Analysis of Fluorescence of DRAQ5 and an N-oxide Derivative (DRAQ5N) in Viable Cells We have sought to exemplify the effect of changes to the structure of a compound of the general form of compound (I) on viable cell staining characteristics. An N-oxide derivative of DRAQ5 (ie DRAQ5N) retains the general structure (I) but has lost overall charge. The change affects the efficiency of the binding potential of the agent in viable cells while retaining fluorescence, cell-permeant properties and nuclear location. FIG. 2h to k show that under equivalent conditions for the detection of nuclear flurorescence in viable human cells, DRAQ5 integrated nuclear fluorescence intensity per nucleus section was approximately 10-fold greater than the value derived for DRAQ5N-treated cells. Previous publications (see references 1–10 below) have described the characteristics of alkylaminoanthraquinone N-oxides and their potential as bioreductive pro-drugs. Thus the N-oxide of DRAQ5 (ie DRAQ5N) described here will share the properties of this class of agents in being capable of bioreductive conversion to DRAQ5. We suggest that the novel fluorescence characteristics of DRAQ5 will provide a marker for cellular bioreductive activity, and by implication hypoxic status, by virtue of DRAQ5N conversion. Thus, the present invention envisages the use of DRAQ5N as a marker for hypoxic cells.

Thus, FIG. 2h to k show simultaneous CLSM capture of transmission (panels h and j) and the corresponding far red/low infra-red fluorescence (panels i and j respectively) images of viable HL60 cells exposed to either 10 μM DRAQ5 or 10 μM DRAQ5N for 1 h.

1. Patterson L H: Anthraquinone anticancer compounds with (disubstituted amino-N-oxide)alkylamino substituent. UK Patent GB2237283, 1989
2. Patterson, L. H. Rationale for the use of aliphatic N-oxides of cytotoxic anthraquinones as prodrug DNA binding agents: a new class of bioreductive agent. Cancer and Metastasis Revs. 12, 119–134, 1993.
3. Patterson, L H, Craven, M R, Fisher, G R and Teesdale-Spittle, P. Aliphatic amine N-oxides of DNA binding agents as bioreductive drugs. Oncology Research 6, 533–538, 1994.
4. Mckeown, S R, Hejmadi, M V, McIntyre, I A, McAleer, J J A and Patterson, L H. AQ4N: an alkylaminoanthraquinone N-oxide showing bioreductive potential and positive interaction with radiation in vivo. Brit J Cancer, 72,76–81.
5. Mckeown, S R, Hejmadi, M V, McIntyre, I A, McAleer, J J A and Patterson, L H. AQ4N: an alkylaminoanthraquinone N-oxide showing bioreductive potential and positive interaction with radiation. Brit J Cancer, 72, 76–81, 1995.
6. Wilson, W R, Denny, W A, Pullen, S M, Thompson, K M, Li, A E, Patterson, L H. Tertiary amine N-oxides as bioreductive drugs: DACA N-oxide, nitracrine N-oxide and AQ4N, Brit J Cancer, 74, S43–47, 1996.
7. McKeown, S R, Friery, O P, McIntyre, I A, Hejmadi, M V, Patterson L H. Evidence for a therapeutic gain when AQ4N or tirapazamine is combined with radiation Brit J Cancer 74, S39–42, 1996
8. Hejmadi, M V, McKeown, M V, Friery, O P, McIntyre, I A, Patterson, L H and Hirst, D G. DNA damage following combination of radiation with the bioreductive drug AQ4N: possible selective toxicity to oxic and hypoxic cells. Brit J Cancer, 73, 499–505, 1996.
9. Smith, P J, Blunt, N J, Desnoyers, R, Giles, Y and Patterson, L H. DNA topoisomerase II dependent cytotoxicity of alkylaminoanthraquinones and their N-oxides. Cancer Chemotherap. Pharmacol, 39, 455–461 (1997)
10. Smith, P J, Desnoyers, R, Blunt, N, Giles, Y and Patterson, L H. Flow cytomeric analysis and confocal imaging of anticancer alkylaminoanthraquinones and their N-oxides in intact human cells using 647 nm Krypton laser excitation. Cytometry, 27, 1, 43–53, 1997.

CLSM Imaging of Dual Fluorochrome Vital Cell Staining

Figure 3A:
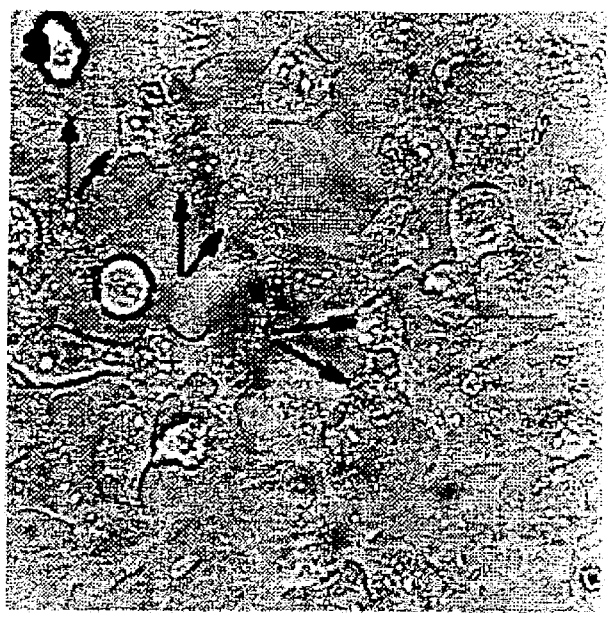
Figure 3B:
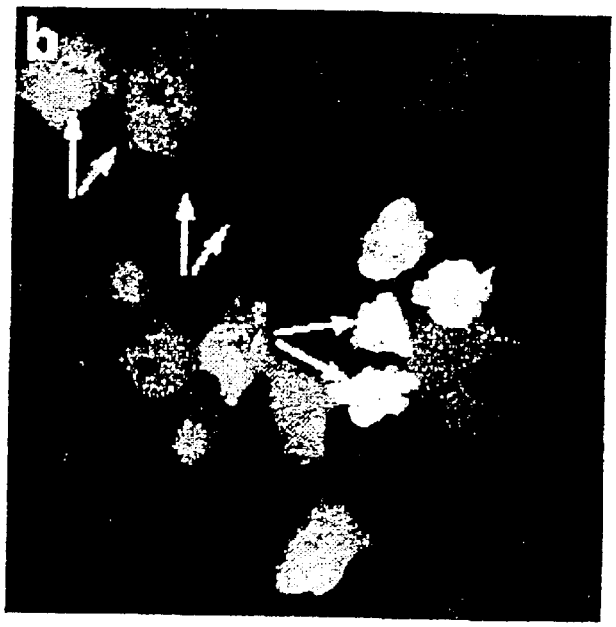
Figure 4A:
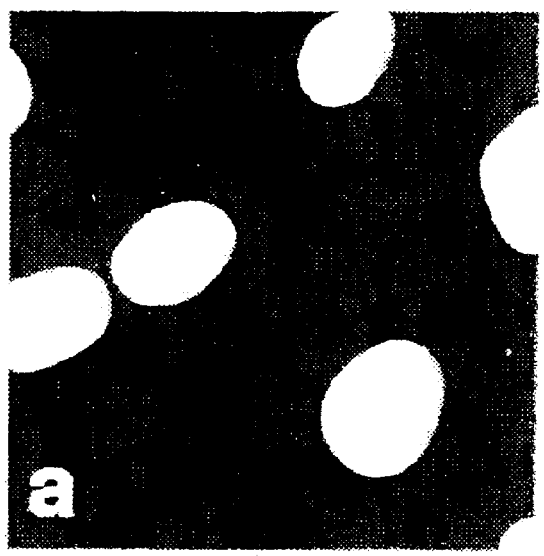
Figure 4B:
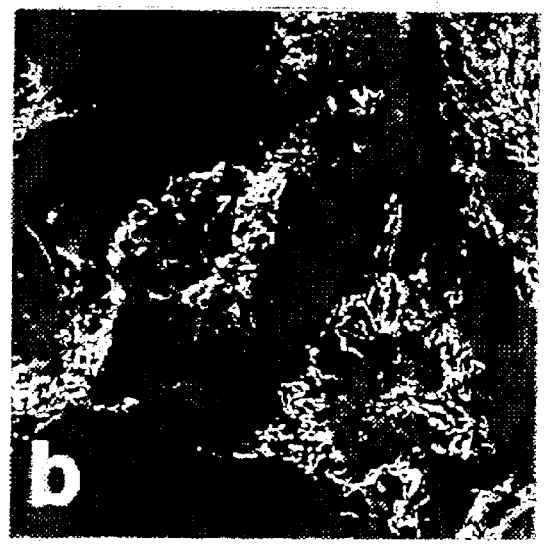
Figure 4C:
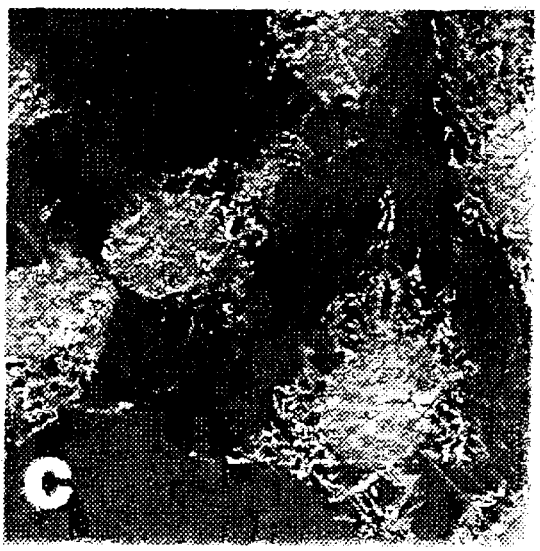

We have sought to demonstrate the spectral separation of the DRAQ5 fluorescence signal from that of other commonly used fluorochromes by using selective excitation. FIG. 3b shows the significant variation in the capacity of the A375 cells for intracellular conversion of FDA by esterase cleavage to the retained form of fluorescein. Imaging the same sample using selective excitation of DRAQ5 clearly demonstrates nuclear morphology (FIG. 3c), while transmission imaging (FIG. 3a) reveals overall cellular form. Triple imaging analysis identifies daughter cell pairs (marked x, y and z by arrows in FIG. 3d). Dual imaging was extended to a vital dye capable of defining cytoplasmic organelles. FIGS. 4a–c shows DRAQ5 (nuclei) and rhodamine 123 (mitochondria) co-labelled cells.

Thus, FIGS. 3a–d show differential excitation of fluorescein and DRAQ5 in viable A375 cells analysed by CLSM. Cells were treated with 10 μM DRAQ5×1 h and subsequently labelled with FDA at 1 μM for 15 min. Panels show the same view imaged as follows: a, transmission image; b 488 nm excitation of fluorescein; c, 647 nm excitation of DRAQ5; d, merged images of a–c encoded blue, green and red respectively. Images are 250×250 μm; pairs of daughter cells are indicated by arrows.

FIGS. 4a–c show images a–c showing the differential excitation of rhodamine 123 and DRAQ5 in viable A375 cells analysed by confocal laser scanning microscopy. Cells were treated with 10 μM DRAQ5×1 h and subsequently labelled with rhodamine 123 at 2 μg/ml for 5 min. Images a and b show the same view with either 488 nm or 647 nm excitation respectively. Image c represents the merged images of a (encoded green) and b (encoded red). Images are 100×100 μm.

EXAMPLE 5

Flow Cytometry Applications of DRAQ5 as a Novel Deep Red/Infra Red Fluorescent DNA-binding Probe Flow cytometry, as used here, is a process for the measurement of the light scatter and fluorescence characteristics of cells or particles passing through a measuring apparatus in a fluid stream in which single cells traverse the focus position(s) of single or multiple laser beams. The time delay in passing through spatially separated focus positions is monitored electronically allowing the cytometer to generate fully correlated multiparameter measurements for multi-beam configurations. Here we demonstrate the use of DRAQ5 in single, dual and triple beam systems in a set of applications using human cells.

Cell Culture

HL60 (human promyelocytic leukaemia cell line) and SUD4 (human B cell lymphoma cell line) were grown as suspension cultures in RMPI medium with 10% foetal calf serum, 1 mM glutamine and antibiotics and incubated at 37° C. in an atmosphere of 5% $CO_2$ in air. For flow cytometry experiments, asynchronously growing suspension cultures were diluted to $2.5–4 \times 10^5$ cells/ml at 2 h prior to drug treatment. Cell cycle-perturbed populations were obtained by treating SUD4 cells with the drug etoposide (VP-16–213) at 0.25 $\mu$M for 18 h. Cells were treated with DRAQ5 and FDA as described above. Cell concentrations were determined using a Coulter counter and cell cycle distribution determined using an algorithm for the normal distibution of fluorescence intensity profiles for fluorochrome stained G1 and G2 cells.

Suspension cultures were analysed by flow cytometry without washing. Human blood was obtained using routine venepuncture of a healthy donor and samples manipulated using-standard haematological procedures for the isolation of mononuclear blood cells and surface antigen recognition using antibody panels (see Table 1).

Footnotes to Table a: Fluorescence detected on PL3 and analysed as pulse area parameter for cell populations gated on the relevant forward-scatter (FSC) and side-scatter (SSC) characteristics. All cell preparations analysed at $2.5 \times 10^5$/ml, unless otherwise indicated, in phosphate buffered saline plus 1% BSA (ie analysis buffer) without (0 min) or with (5 or 120 min exposure) 20 $\mu$M DRAQ5.

b: Preparation 1: Cells derived from cell culture of the SUD4 human follicular B cell lymphoma line and resuspended in analysis buffer. Parallel analysis of samples using conventional ethidium bromide staining of RNase A-digested permeabilised cells yielded G1=34.9%, S phase=48.0%, G2/M=17.1% for asynchronous cultures, and G1=0.6%, S phase=55.3%, G2/M=44.0% for late cell cycle-arrested cells obtained by treating cells with the cytotoxic drug VP-16 (0.25 $\mu$M×18 h). Quantitative analysis of DNA content of G1 (SUD4): G1 (normal diploid lymphocytes) gave a ratio of 1.083.

c: Preparation 2: As for Preparation 1 but processed for surface antigen analysis using directly labelled antibodies: anti-CD54-FITC (detected on FL1 parameter), anti-CD19-PE (detected on FL2 parameter).

d: Preparation 3: Ficoll gradient-separated viable mononuclear blood cells from normal donor. Sample obtained by routine venepuncture (ratio lymphocytes:monocytes=11.5:1) and resuspended in analysis buffer.

TABLE 1

FACScan ™ (Cytometer C) flow cytometric analysis of DRAQ5-labelled human cells

| Cell preparation & DRAQ5 exposure (min) | Mean fluorescence intensity (± sd) of gated population[a]: | | | |
|---|---|---|---|---|
| | SUD4 cells | Lymphocytes | Monocytes | Granulocytes |
| Preparation 1: viable cultured cells[b] | | | | |
| 0 | 1.3 ± 6.8 | | | |
| 5 | 499.4 ± 143.3 | | | |
| 5 | 532.4 ± 148.3 | | | |
| 120 | 645.1 ± 177.7 | | | |
| 0 (0.25 $\mu$M VP-16) | 6.0 ± 16.6 | | | |
| 5 (0.25 $\mu$M VP-16) | 891.8 ± 126.4 | | | |
| Preparation 2: viable cultured cells, surface antigen analysis[c] | | | | |
| 0 | 5.2 ± 13.8 | | | |
| 5 | 564.3 ± 147.2 | | | |
| 0 (0.25 $\mu$M VP-16) | 13.4 ± 21.6 | | | |
| 5 (0.25 $\mu$M VP-16) | 902.7 ± 117.1 | | | |
| Preparation 3: Ficoll gradient-isolated viable mononuclear blood cells[d] | | | | |
| 0 | | 0.8 ± 4.6 | 1.7 ± 5.7 | |
| 5 | | 227.4 ± 24.5 | 302.9 ± 25.4 | |
| 5 (4.8 × $10^5$/ml) | | 215.9 ± 26.3 | 301.8 ± 24.3 | |
| 5 (7.5 × $10^5$/ml) | | 234.1 ± 27.0 | 311.0 ± 30.9 | |
| 120 | | 299.1 ± 23.9 | 342.2 ± 22.4 | |
| Preparation 4: Preparation 3 plus surface antigen analysis[e] | | | | |
| 0 | | 0.0 ± 0.1 | 0.0 ± 0.1 | |
| 5 | | 261.6 ± 26.3 | 317.9 ± 27.3 | |
| Preparation 5: Whole blood, viable cells surface antigen analysis[f] | | | | |
| 0 | | 0.0 ± 0.2 | 0.1 ± 1.1 | 0.1 ± 2.1 |
| 5 | | 257.3 ± 35.0 | 274.6 ± 41.0 | 248.4 ± 35.9 |
| Preparation 6: Preparation 5 but cells lysed and fixed[g] | | | | |
| 0 | | 0.0 ± 0.3 | 0.0 ± 0.9 | 0.1 ± 3.0 |
| 5 | | 228.5 ± 28.5 | 240.2 ± 28.1 | 254.3 ± 31.1 | e: Preparation 4: As for preparation 3 but processed for surface antigen analysis using anti-CD45-FITC.

f: Preparation 5: Whole blood from normal donor processed for surface antigen analysis, analysed as viable cells using anti-CD45-FITC positivity as the FL1 parameter master trigger to exclude RBCs. Gated populations of 25.5% lymphocytes, 13.3% monocytes, 61.2% granulocytes g: Preparation 6: As for preparation 5 but after processing for surface antigen analysis, cells fixed and RBCs lysed in FACSLyse™ and re-suspended in analysis buffer. FSC parameter as master trigger. Gated populations of 43.7% lymphocytes, 9.7% monocytes, 46.6% granulocytes.

Flow Cytometry

Cells were analysed using one of four flow cytometers according to the excitation requirements.

Cytometer A: Single beam high power 647 nm krypton laser excitation: The system was a custom-built cytometer and incorporated an Innova 3000K krypton laser (Coherent Corp., Palo Alto, Calif., USA) tuned to the 647 nm line. Forward light scatter, 90° light scatter and fluorescence emissions were collected for $1\times10^4$ cells using the 90° light scatter parameter as the master signal. The optical system permitted the analysis of various fluorescence emission wavelengths including: >715 nm (termed low infra-red) and, as reported here >780 nm fluorescence (infra-red). Forward and 900 light scatter were analysed for the identification of cell debris. Laser power was set at 200 mW and linear amplifiers were used for the fluorescence signals. The analysis optics included a 675 nm cold dichroic mirror, ambient laboratory temperature was approximately 12° C. and the sheath reservoir was maintained at 100° C. Filters were supplied by Melles Griot. Median, mean and mode parameters were calculated for the distribution of fluorescence intensity values throughout a given cell population. In all experiments, median and mean values produced very similar results. Median values alone are reported since this parameter is less affected by the presence of highly fluorescent cells beyond the upper limit for quantification.

Cytometer B: Dual beam low power 633 nm/high power 488 nm laser excitation: The system was a FACS 440 cell sorter (Becton Dickinson Inc., Cowley, UK) incorporating a Spectra Physics argon ion laser (max 500 mW output), tuned to the 488 nm line (100 mW output), and a secondary Spectra Physics 156 helium-neon laser emitting at 633 nm (emitting <5 mW), with a temporal beam separation of about 30 μsec. Forward light scatter, 90° light scatter and fluorescence emissions were collected for $1\times10^4$ cells using the forward light scatter parameter as the master signal from the primary 488 nm beam, while side scatter was collected through a 488/10 nm band-pass filter. The analysis optics included: i) a cold dichroic mirror (transmitting >675 nm), ii) fluorescence from fluorescein excited by the 488 nm beam detected at a PMT guarded by a 535/15 nm band-pass filter with no signal delay, and iii) a red-sensitive PMT with an appropriate delay, additionally guarded by a 620 nm long-pass filter, to detect the transmitted beam of DRAQ5-associated fluorescence at wavelengths beyond 675 nm (high-red and extending into the infra red region of the spectrum). Forward and 90° light scatter were analysed to exclude any cell debris. All parameters were acquired at 256 channel resolution with Consort 30 software (Becton Dickinson) and subsequently analysed with WinMDI software (J.Trotter, La Jolla, Calif.). The system employed the same analysis optics when used in the single 488 nm beam mode but with no signal delay for the red-sensitive PMT.

Cytometer C: Single beam, low power 488 nm laser excitation: The system was a FACScan (Becton Dickinson Inc., Cowley, UK) incorporating an argon ion laser (max 15 mW output), tuned to the 488 nm line. Forward light scatter, 90° light scatter and fluorescence emissions were collected for $1\times10^4$ cells using the forward light scatter parameter as the master signal. The standard analysis optics provided the FL1 (blue)/FL2 (green)/FL3 (red) PMT parameters with pulse analysis performed on the FL3 originating signals.

Cytometer D: Triple beam medium power 633 nm/medium power 488 nm/medium power multiline-UV laser excitation:

The system was a FACS Vantage cell sorter (Becton Dickinson Inc., Cowley, UK) incorporating a Coherent Enterprise II laser simultaneously emitting at multiline UV (350–360 nm range) and 488 nm wavelengths with the beams made non-co-linear using dichroic separators. Beam-combining optics were used to align the UV beam with that emitted by a Spectra Physics 127-35 helium-neon laser (max 35 mW output) emitting at 633 nm with a temporal separation of about 25 μsec from that of the primary 488 nm beam. Forward light scatter, 90° light scatter and fluorescence emissions were collected for $1\times10^4$ cells using the forward light scatter parameter as the master signal from the primary 488 nm beam, while side scatter was collected through a 488/10 nm band-pass filter. The analysis optics were: i) primary beam-originating signals analysed at FL1 (FITC filter; barrier filter of 530/30 nm) after transmission at SP610 and SP560 dichroics, or at FL2 (barrier filters of 585/42 nm or 575/26 nm) after transmission at SP610 and reflection at SPS60 dichroics, or at FL3 (barrier filter of LP715 nm) after reflection at a SP610 dichroic; ii) delayed beam-originating signals analysed at FL4 (barrier filter of LP695 nm) or at FL5 (barrier filter of DF424/44 nm) after transmission or reflection at a LP640 dichroic respectively. Forward and 90° light scatter were analysed to exclude any cell debris. All parameters were analysed using CellQuest software (Becton Dickinson).

Whole Cell Fluorescence Detected by Flow Cytometry

Despite DRAQ5 excitation being optimal at the 647 nm laser wavelength, preliminary studies indicated that the probe could be sub-optimally excited at lower wavelengths, including multi-line UV 488 nm, 514 nm and 633 nm. Here we have sought to assess DRAQ5 as a DNA probe for use in flow cytometry by comparing the four different cytometer configurations:

Cytometer A: Single-beam high power 647 nm krypton laser excitation.

Cytometer B: Dual-beam low power 633 nm/high power 488 nm laser excitation.

Cytometer C: Single-beam low power 488 nm laser excitation.

Cytometer D Triple-beam medium power 633 nm/medium power 488 nm/medium power multiline-UV laser excitation.

Figure 5:
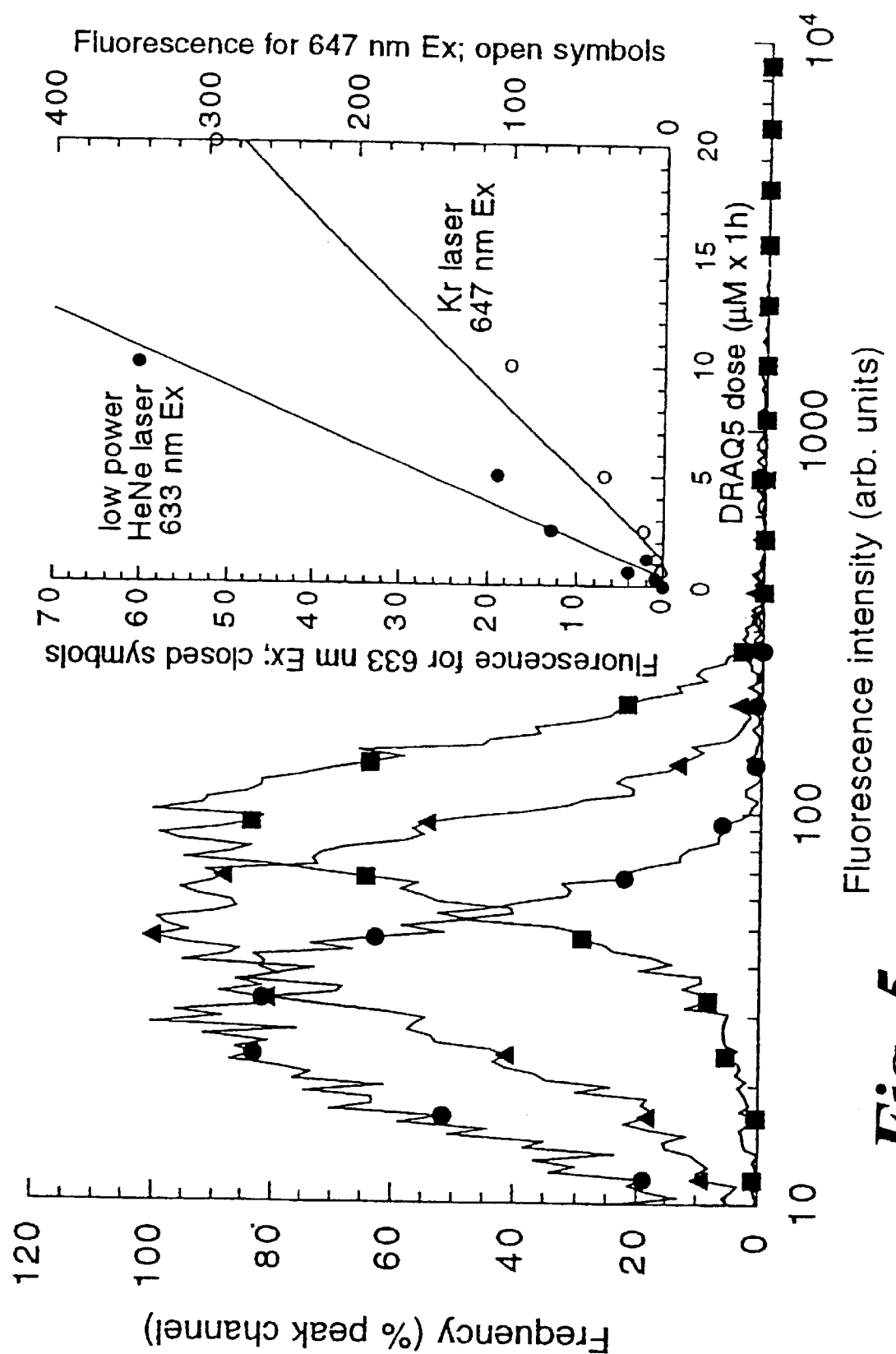

FIG. 5 shows that using a low power HeNe laser (Cytometer B), complete separation does not occur for autofluorescence and DRAQ5 signals for viable HL-60 cells treated with a low, non-saturating DRAQ5 concentrations. Further studies (data not shown) indicate that complete separation could be achieved after a two hour incubation with 20 μM DRAQ5. However even under these limiting excitation conditions the 633 nm derived DRAQ5 signal shows a clear linear dose-response (see inset to FIG. 5) down to approximately 2.5 μM, comparable with the linearity obtained for optimal 647 nm excitation (using Cytometer A) and detection at wavelengths >780 nm.

Figure 6:
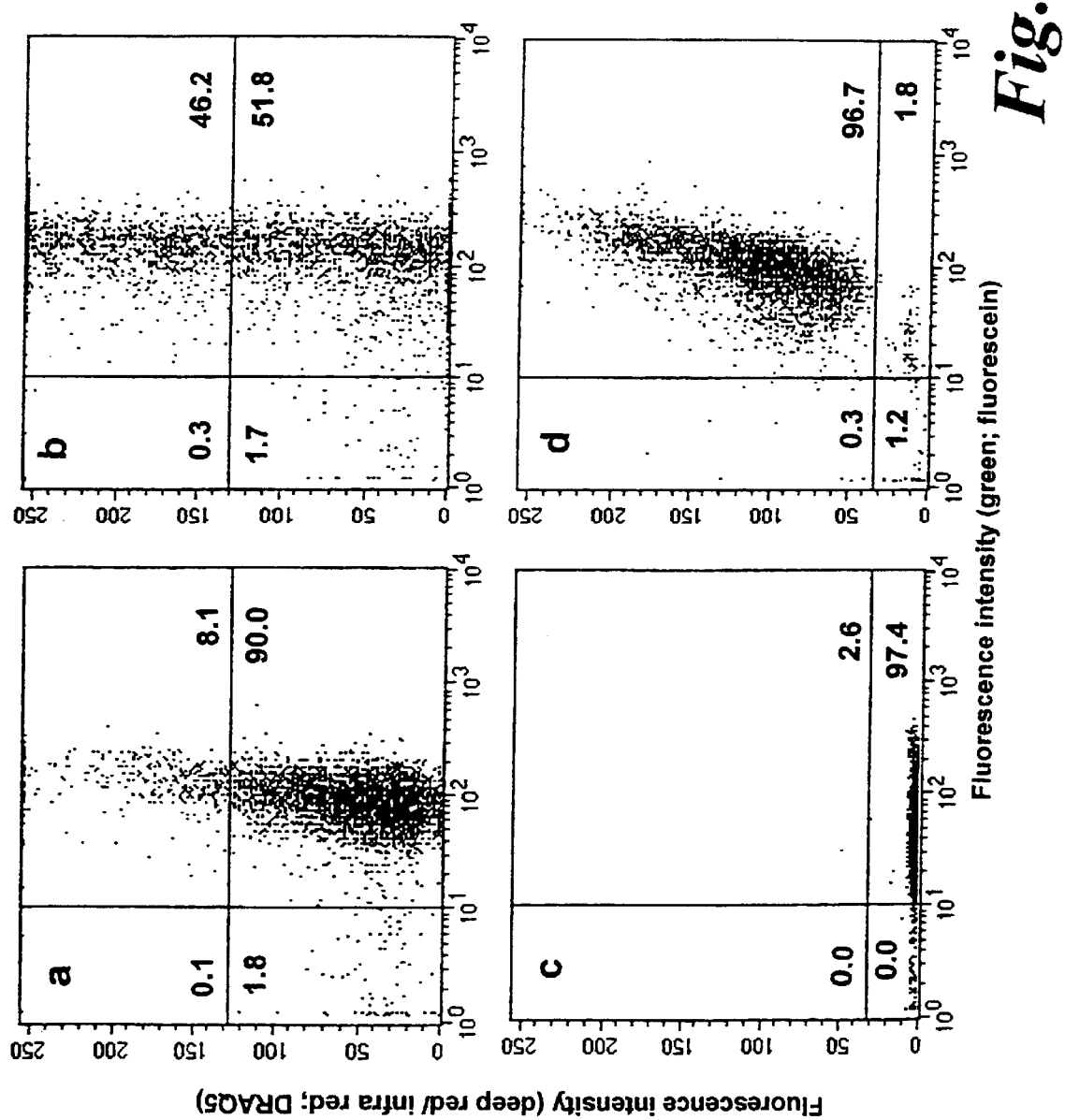

FIG. 6 a and b show that a low power HeNe laser (Cytometer B) can be used to identify DRAQ5-associated fluorescence in fluorescein-loaded cells analysed in a dual beam configuration. FIG. 6c and d shows co-excitation of DRAQ5 and fluorescein is possible using a single beam of 488 nm wavelength (Cytometer B). There is clear separation of signals, due to the distinct, non-overlapping spectra, despite the low intensity signal derived from sub-optimal excitation of DRAQ5.

Figure 7:
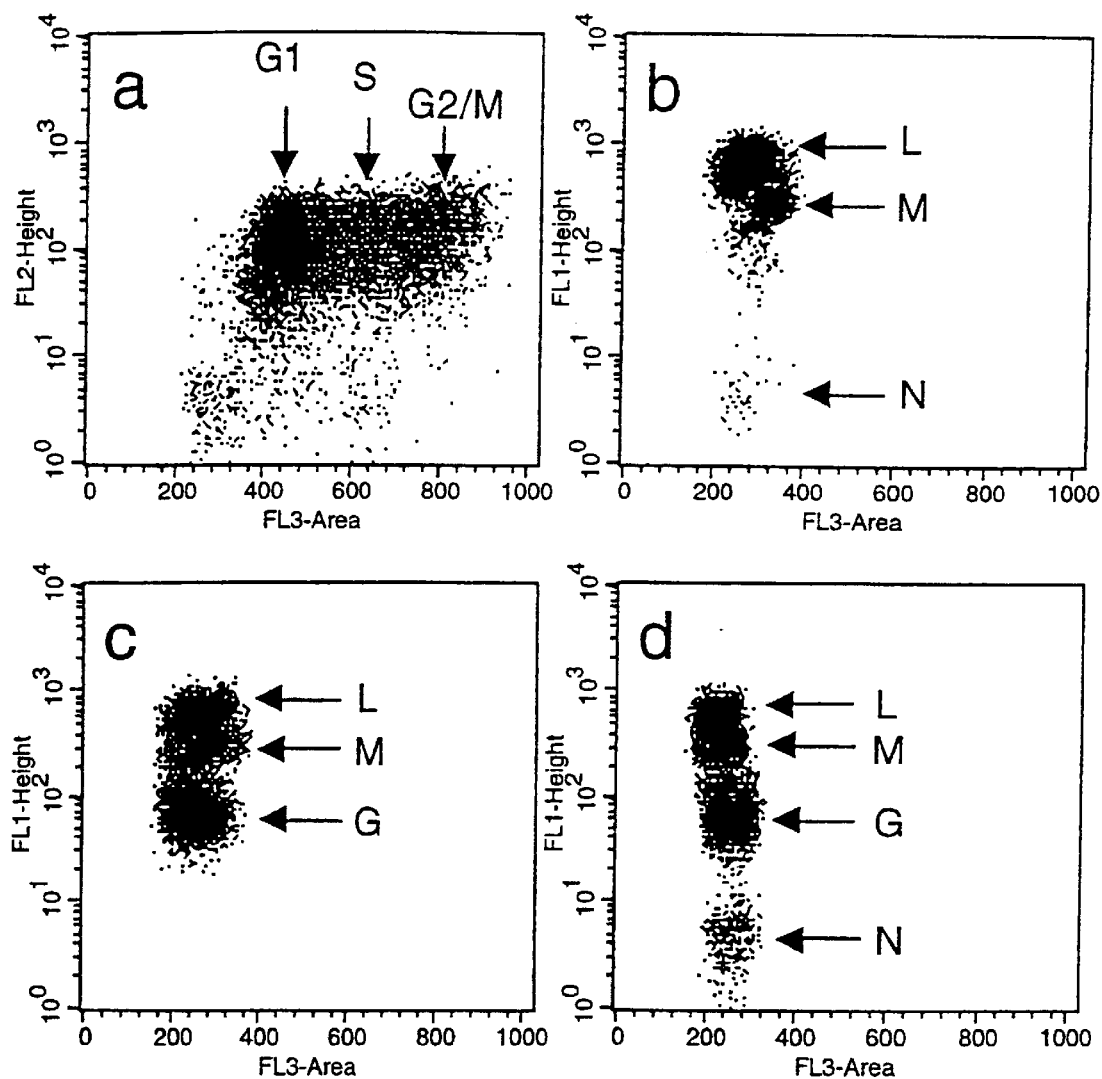

We have sought to demonstrate the utility of DRAQ5 in a single beam cytometer (ie FACScan™; Cytometer C). FIG. 7 a–d shows typical results demonstrating the ability of DRAQ5 to identify nucleated cells in complex populations. FIG. 7a shows the detection of cell cycle distribution versus cell is surface antigen expression for intact cells. FIG. 7b shows the discrimination of subsets according to staining potential while FIGS. 7c and 7d demonstrate the application of DRAQ5 in detecting nucleated cells in whole blood and lysed blood. Factors relating to the ability of DRAQ5 to stain nuclei are analysed in the Table. Using viable cultured asynchronous cells (Preparation 1) DRAQ5 rapidly stained cells in a reproducible manner and generated fluorescence distinct from the autofluorescence background. The large sd values derive from the spread of cells throughout the cell cycle. The mean value reflects mean cellular DNA content as evidenced by the 1.7-fold increase for G2 arrested populations. The processing of cells for surface antigen analysis (Preparation 2) does not affect the above characteristics. The isolation of intact mononuclear blood cells (Preparations 3 and 4) yields samples which can be stained within a convenient cell density range and be processed for surface antigen analysis. In Preparations 3 and 4 we have consistently observed an enhanced staining potential of monocytes versus lymphocytes (1.14–1.4 fold) indicating that viable cell staining potential may be used as a factor for subpopulation discrimination. The results for whole blood show that nucleated cells (including granulocytes) can be stained to a similar degree in the presence (Preparation 5) of red blood cells (RBCs) or following RBC lysis and mild fixation (Preparation 6).

Figure 8:
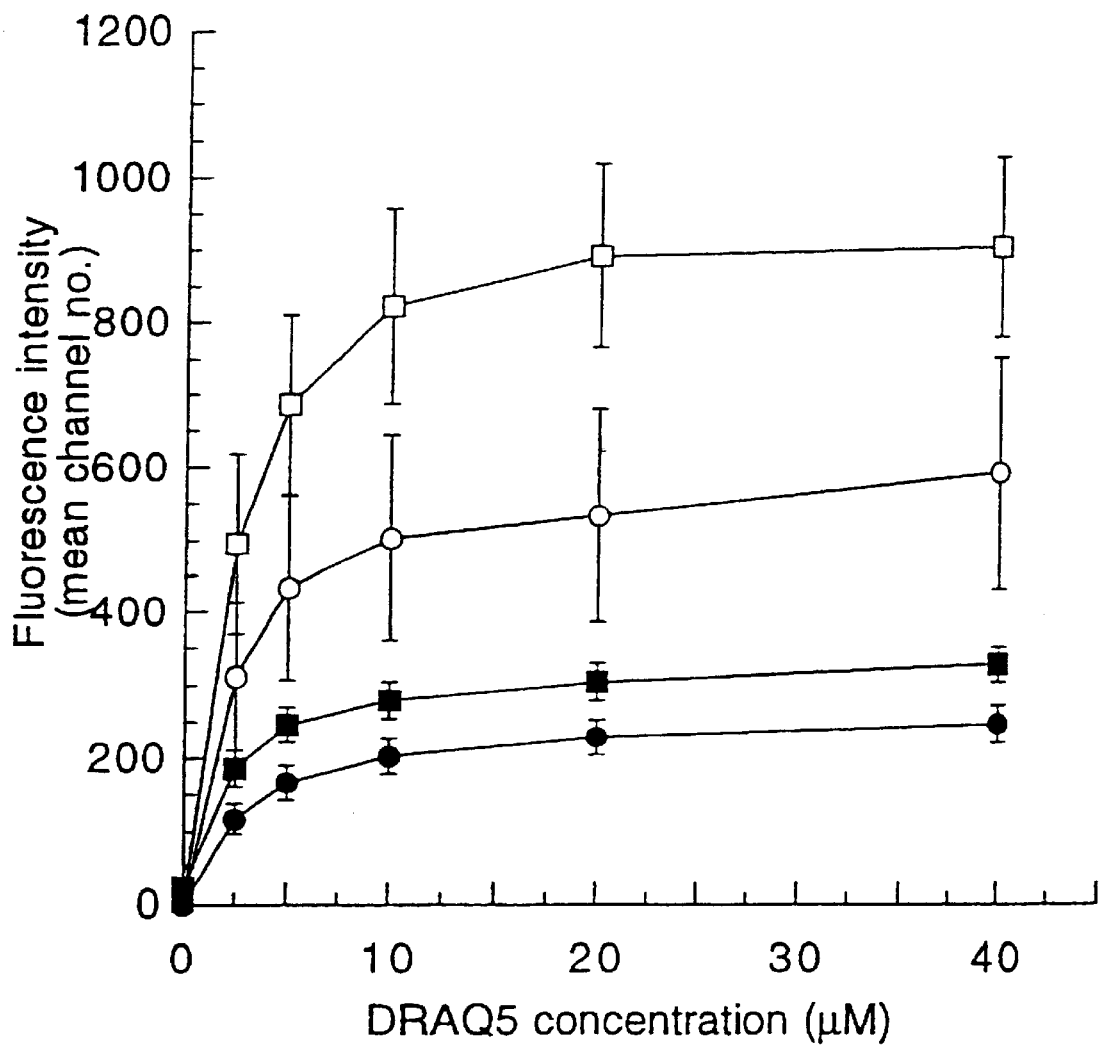
FIG. 8 shows single beam flow cytometric quantification of fluorescence intensity of cultured and blood-derived human cells exposed to DRAQ5.
Figure 12A:
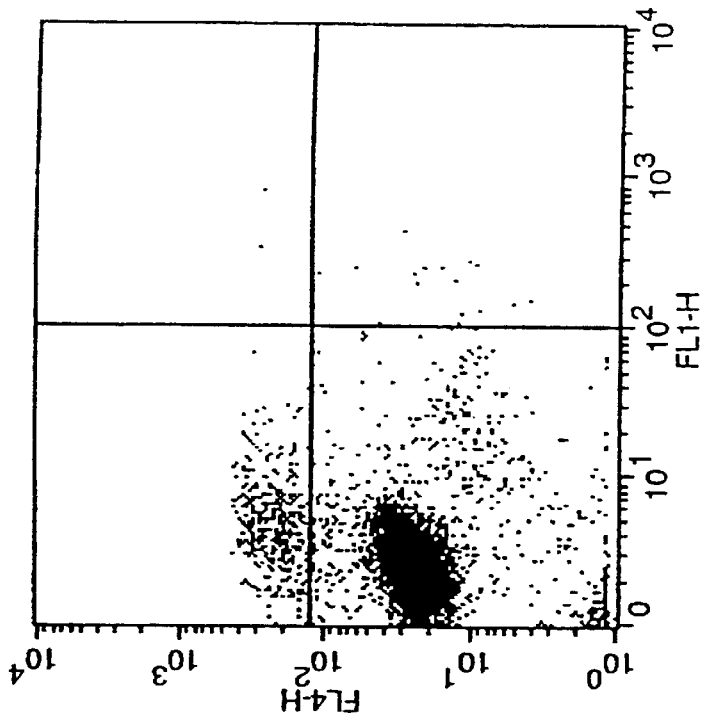
Figure 12B:
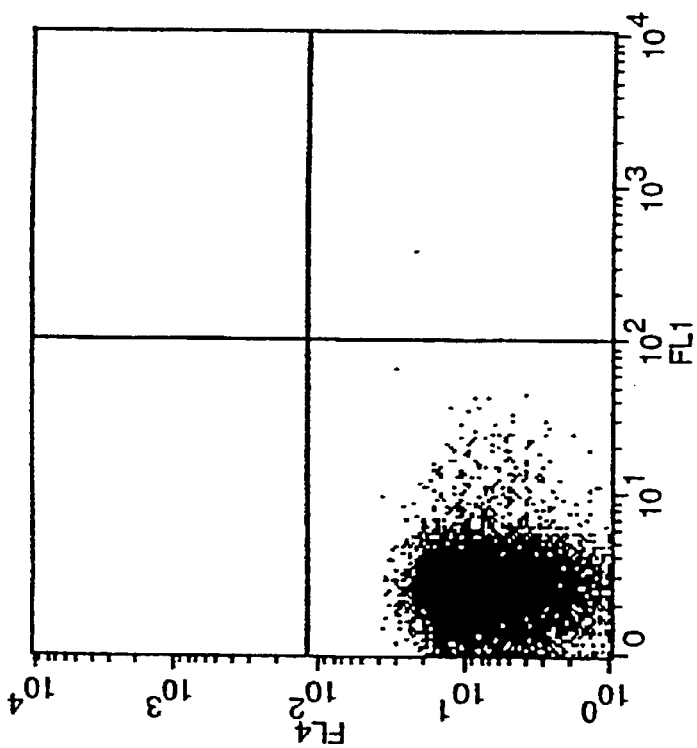
Figure 12D:
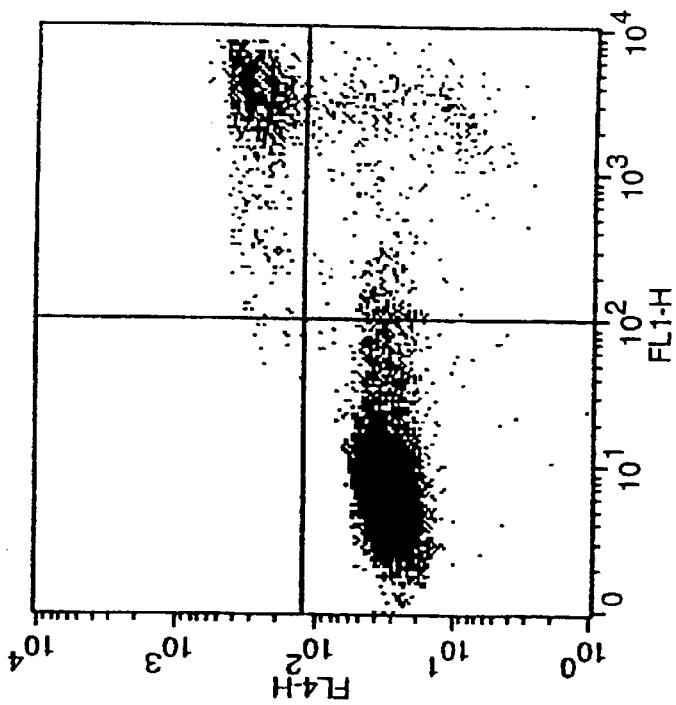
Figure 12C:
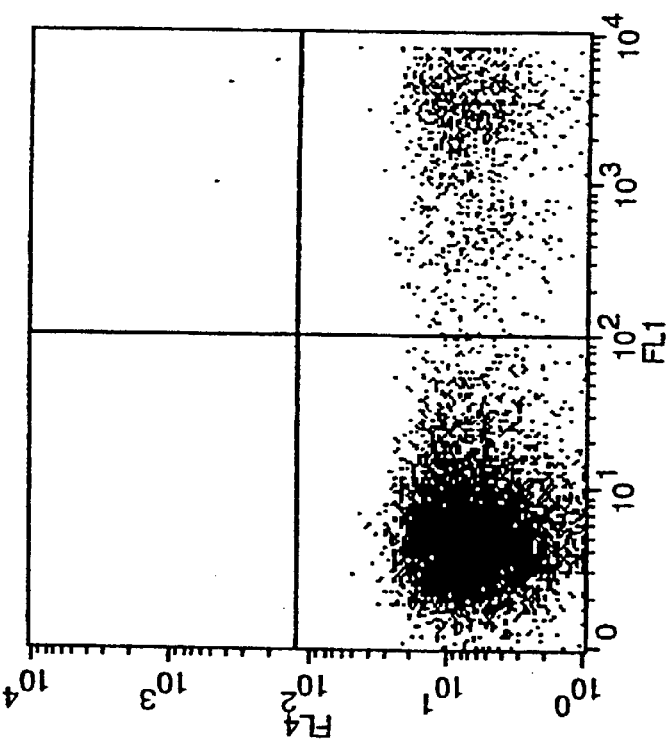
Figure 13B:
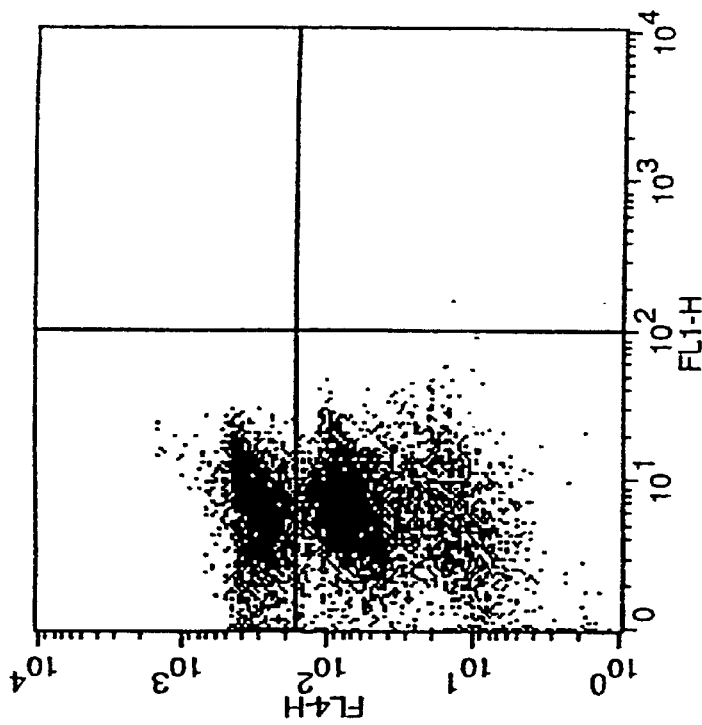
Figure 13A:
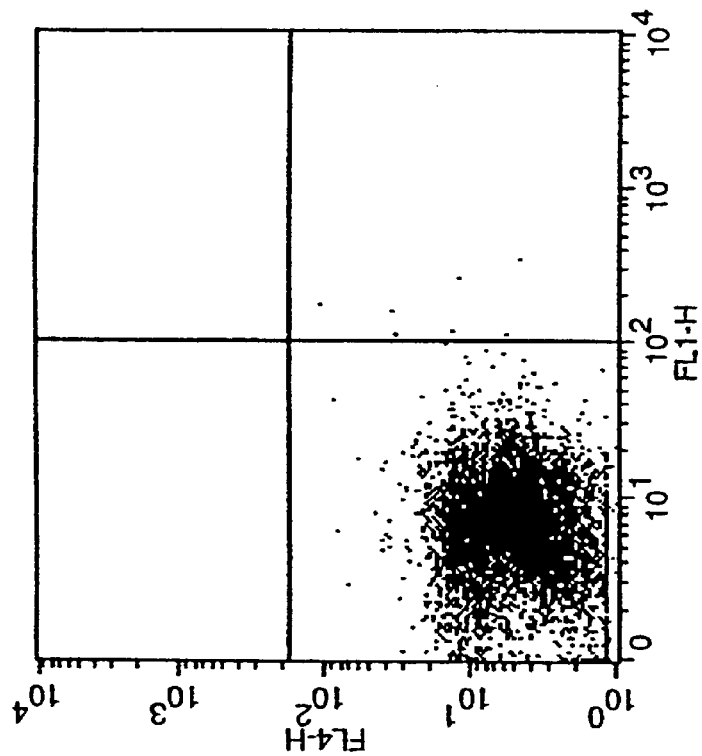

FIG. 8 summarises the DRAQ5 concentration-dependent differences in DRAQ5 staining for viable cell populations obtained using Preparation methods 1 and 2 (see footnote to Table). The populations show similar titration curves with saturation occurring in a manner which reflects relative DNA content (for a given cell type, eg SUD4) or nuclear staining potential (eg lymphocytes versus monocytes) at concentrations of ≧10 μM.

FIG. 9 demonstrates the utility of DRAQ5 for the detection of the cell cycle specific expression of an intracellular protein, in fixed cells, detected using fluorochrome-tagged antibodies activated by 488 nm (FITC) and multiline-UV wavelengths (Cytometer D). FIGS. 10a–f show that in a triple beam configuration (Cytometer D) it is possible to demonstrate DRAQ5 fluorescence activated by two separate beams with discrimination on a third for the monitoring of relatively rare cell cycle events such as high cyclin B1 expression in G2/M of asynchronous cultures.

Thus, FIG. 5 shows flow cytometric analyses of DRAQ5 accumulation, for a one hour exposure period, in viable HL60 cells. Frequency distribution histograms are for low power 633 nm wavelength excitation using Cytometer B. Symbols: ○, ▲ and ■ represent 0, 5 and 10 μM DRAQ5 respectively. Inset: Linearity of DRAQ5 dose-response, using two different Cytometers (namely B and A with correlation coefficients of 0.96 and 0.97 for 633 nm and 647 nm excitations respectively).

FIGS. 6a to d show dual beam flow cytometric analysis (Cytometer B) for the detection of DRAQ5-associated fluorescence in fluorescein-labelled viable HL60 cells. Representative flow cytometric bivariate plots of green (FL2-height; fluorescein) versus deep red/low infra red (FL1-height; DRAQ5) whole cell fluorescence signals. Panels a and b show dual beam excitation of fluorescein (488 nm) and DRAQ5 (low power 633 nm). Panel: a, FDA (0.2 μM for 10 min alone); b, cell pretreated with 5 μM DRAQ5 for 1 h prior to FDA treatment. Panels c and d repeat the same cell treatment conditions except for the use of single beam excitation at 488 nm for fluorescein and DRAQ5. Numbers indicate the percentage of gated events within the quadrant regions.

FIGS. 7a to d show single beam flow cytometric analysis of (Cytometer C) of DRAQ5 fluorescence (FL3-area) versus antibody fluorescence (FL2-height monitoring phycoerythrin-labelled anti-CD19 or FL1-height monitoring FITC-labelled anti-CD45) for cultured and blood-derived human cells. Cell suspensions (2.5×10$^5$/ml) were maintained in phosphate buffered saline containing 1% bovine serum albumin. Human blood mononuclear cell subpopulations, obtained using standard Ficoll gradient separation, were identified and gated according to their forward- and side-light scatter characteristics. Doublets were excluded by pulse analysis gating on normal FL3-area versus FL3-width parameter values. Panel a: cultured asynchronous SUD4 lymphoma cells. Panel b: blood mononuclear cell subpopulations, obtained using standard Ficoll gradient separation. Panel c: whole blood (triggered on CD45+events). Panel d: lysed whole blood. Arrowed subpopulations: G1 S and G2/M represent cell cycle phases; L, lymphocytes; M, monocytes; G, granulocytes; N, nuclei lacking plasma membranes.

FIG. 8 shows single beam low cytometric quantification (Cytometer C) of fluorescence intensity of cultured and blood-derived human cells exposed to DRAQ5 at room temperature for 5 min. Data are mean values (±SD) and represent results from a typical experiment. Symbols: ○, cultured asynchronous SUD4 lymphoma cells; □, SUD4 cells exposed to 0.25 μM VP-16 for 18 h to arrest cells in S phase and G2 of the cell cycle; ●, lymphocytes; ■, monocytes.

FIG. 9 shows dual beam flow cytometric analysis (Cytometer D) of the cell cycle specific expression of cyclin B1. Fixed, RNaseA-digested and DRAQ5-stained (FL3; 488 nm excitation) SUD4 cells were obtained from an asynchronous culture exposed to 0.25 μM VP-16 for 18 h to accumulate cells in G2/M. G2/M phase-expressed cyclin B1 protein was monitored by indirect immunofluorescence using AMCA-labelled second antibody (FL5-height; multi-line UV excitation) to detect the binding of anti-cyclin B1 (GNS1) mouse monoclonal IgG. Panels a and c show antibody controls (non-specific IgG plus second antibody). Panels b and d show results for specific antibody plus second antibody. Antibodies were obtained from Santa Cruz Biotechnology Inc. Arrowed subpopulations: G1, S and G2/M represent cell cycle phases; unlettered arrow shows expected position of cells expressing high levels of cyclin B1 and located in G2/M of the cell cycle.

FIGS. 10a to f show triple beam flow cytometric (Cytometer D) analysis of DRAQ5-stained fixed and RNase A digested asynchronous SUD4 lymphoma cells. DRAQ5 fluorescence (pulse height) monitored by FL3 (488 nm excitation) and FL4 (633 nm excitation). Cell cycle-independent Cdc2 protein and the G2/M phase-expressed cyclin B1 protein were monitored by indirect immunofluorescence using FITC-labelled second antibody (FL1-height; 488 rim excitation) to detect the binding of anti-Cdc2 p34 (H-297) rabbit polyclonal IgG, and AMCA-labelled second antibody (FL5-height; multiline UV excitation) to detect the binding of anti-cyclin B1 (GNS1) mouse monoclonal IgG. Antibodies were obtained from Santa Cruz Biotechnology. Panels: a and b, DNA versus Cdc-2 p34; c and d, DNA versus cyclin B1; e and f, DNA histograms for blue and red excitation wavelengths respectively. Arrowed subpopulations: G1, S and G2/M represent cell cycle phases; HCyB, high cyclin B1 expressing cells located in G2/M of the cell cycle.

Flow Cytometric Analysis of Multi-line UV Excitation of DRAQ5 Stained Cells

The absorbance peaks noted for wavelengths <400 nm suggest that chromophore excitation at near UV wavelengths should be possible (data not shown). It has been demonstrated that DRAQ5-stained nuclei of living cells can be excited in the near-UV region of the spectrum as shown by the use of multi-line UV flow cytometry (Cytometer D; FIGS. 11a–c). Although UV-excitation is less efficient than at 647 nm wavelength (FIG. 11b) and detection require increased photomultiplier signal amplification, fluorescence intensities clearly reflect cellular DNA content distribution (FIG. 11c). This demonstrates that in triple beam combinations, DRAQ5 can provide a DNA discriminating signal derived from UV, and visible range excitation wavelengths.

FIGS. 11a–c show the 488 nm (panel a), 647 nm (panel b), or multi-line UV (350–360 nm range; panel c) excitation of DRAQ5 in intact SUD4 lymphoma cells for emission at >695 nm wavelengths and analysed by multi-beam flow cytometry (Cytometer D). Bold lines reflect the cellular DNA content of DRAQ5-stained cells; feint lines represent non-stained control cells; dotted lines represent reference allophycocyanine (APC) stained reference micro-beads used as 647 nm excitable standards.

EXAMPLE 6

Differential Cellular Accumulation of an N-oxide Derivative of DRAQ5 (DRAQ5NO) in the Discrimination of Intact and Dead Cells The ability to discriminate intact viable cells from those undergoing the various stages of cell death can be achieved through the differential cellular accumulation of chemical probes including certain fluorochromes. A particular type of cell death, termed apoptosis, has discernible early stages which can occur in intact cells. Discrimination is used extensively in both biological and clinical assays. For example flow cytometric assays may allow for the identification, quantification, analysis, preparation or exclusion of cell subsets. Probe uptake and retention is dependent upon multiple factors, including the integrity of the plasma membrane (eg affecting probe entry) aid the intracellular behaviour of the probe (eg probe binding to nuclear DNA). Current fluorometric assays for cell death can use the ability of intact viable cells to remain unstained by excluding the probe (eg the fluorescent DNA stain propidium iodide), while cells with compromised membranes allow access of the probe to nuclear DNA. Cells undergoing the early stages of apoptotic cell death can be identified by the cell surface binding of the fluorochrome-tagged chemical, Annexin V, but show no loss of membrane integrity. The later stages of cell death and apoptosis, when the plasma membranes become disrupted, are associated with high Annexin V-binding and high propidium iodide DNA-staining.

Here we exemplify the use of an N-oxide derivative of DRAQ5 (DRAQ5NO) providing an enhancement to live-dead cell discrimination. DRAQ5NO is capable of entering into and being retained by intact viable cells at a low level, providing a positive discrimination for intact cells. In combination with a secondary probe (eg Annexin V) there is enhanced discrimination of the stages in the progression of cells through the process of cell death or apoptosis. The four stages, according to the staining patterns are:

stage 1: DRAQ5NO positive/Annexin V negative (intact viable cells)

stage 2: DRAQ5NO positive/Annexin V positive (early stage apoptotic cells)

stage 3: DRAQ5NO high positive/Annexin V positive (late stage apoptotic/dead cells)

stage 4: DRAQ5NO negative/Annexin V positive (non-nucleated cellular debris)

FIGS. 12a–d and FIGS. 13a–d illustrate examples, using a human B cell lymphoma cell line capable of progression through apoptosis in response to the anticancer drug VP-16 (etoposide) for an 18 h exposure to 0.25 $\mu$M. Cells were prepared by standard methods for Annexin V-FITC binding, simultaneously exposed to 50 $\mu$M DRAQ5NO and then diluted 1:5 in phosphate buffered saline prior to flow cytometric analysis using Cytometer D. The instrument was used in a dual laser mode with 488 nm wavelength excitation of FITC (monitored by parameter FL1-H) and 633 nm wavelength excitation of DRAQ5NO (monitored by parameter FL4-H). FIGS. 12a–d show the combinations of reagent treatments (Anx=Annexin V-FITC; AQ5N=the N-oxide derivative of DRAQ5) for control cells and FIGS. 13a–d show the same combination of reagents for VP-16 (i.e. VP) treated cultures. The results show the low level of DRAQ5NO staining achieved in stage 1 populations and the increased level in stage 3 cells. The frequency of cells which are Annexin V positive is increased by VP-16 treatment but comprise three populations (stages 2–4) discernible using the quadrant analysis shown in the plots. The enhancement provided by the use of DRAQ5NO is with respect to two features. First, the advantageous spectral properties of the DRAQ5 derivative allowing for the separation of the probe excitation events by the use of two lasers and/or the greatly reduced spectral overlap of the probe emission signals. Second, the positive discrimination of intact cells from non-nucleated cellular debris.

What is claimed is:

1. A fluorescent complex comprising a nucleic acid and a compound of the following formula:

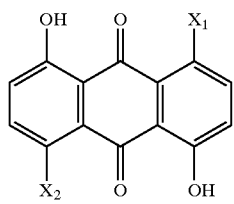

wherein each of $X_1$ and $X_2$ are independently NH—A—$NR^1R^2$, and wherein A is a $C_{2-8}$ alkylene group and $R^1$ and $R^2$ are independently selected from hydrogen, $C_{1-4}$ alkyl, $C_{2-4}$ hydroxyalkyl and $C_{2-4}$ aminoalkyl, or $R^1$ and $R^2$ together form a $C_{2-6}$ alkylene group which with the nitrogren atom to which $R^1$ and $R^2$ are attached forms a heterocyclic ring, and wherein the compound (I) is optionally in the form of an acid salt derived from an organic or inorganic acid.

2. A complex according to claim 1, wherein the nucleic acid is DNA.

3. A complex according to claim 2, wherein the DNA is present in a living cell.

4. A method of analysing a cell or biological material containing nucleic acid, comprising the steps of:

a) preparing a biologically compatible solution containing a compound of the formula (I):

wherein each of $X_1$ and $X_2$ are independently NH—A—$NR^1R^2$, and wherein A is a $C_{2-8}$ alkylene group and $R^1$ and $R^2$ are independently selected from hydrogen, $C_{1-4}$ alkyl, $C_{2-4}$ hydroxyalkyl and $C_{2-4}$ aminoalkyl, or $R^1$ and $R^2$ together form a $C_{2-6}$ alkylene group which with the nitrogen atom to which $R^1$ and $R^2$ are attached forms a heterocyclic ring, and wherein the compound (I) is optionally in the form of an acid salt derived from an organic or inorganic acid;

b) treating the cell or biological material with the biologically compatible solution;

c) exciting the compound (I) in the treated cell or biological material with a light source; and d) detecting the emitted fluorescence signal.

5. A method according to claim 4, wherein the light source provides one or more wavelengths in the spectral region of the wavelength(s) of maximum absorption of compound (I).

6. A method according to claim 4, wherein the compound (I) is present in the cell or biological material with one or more other fluorochromes or light-emitting compounds.

7. A method according to claim 6, wherein the fluorochromes emit in the UV or the visible region of the spectrum.

8. A method according to claim 6, wherein the one or more other compounds are used to detect Annexin V binding.

9. A method according to claim 6, further comprising the step of flow cytometric analysis.

10. A method of forming a DNA dye complex comprising combining a compound of the following formula:

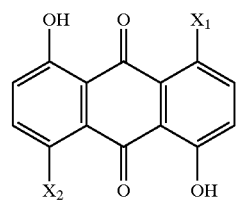

wherein each of $X_1$ and $X_2$ are independently NH—A—$NR^1R^2$ and wherein A is a $C_{2-8}$ alkylene group and $R^1$ and $R^2$ are independently selected from hydrogen, $C_{1-4}$ alkyl, $C_{2-4}$ hydroxyalkyl and $C_{2-4}$ aminoalkyl, or $R^1$ and $R^2$ together form a $C_{2-6}$ alkylene group which with the nitrogen atom to which $R^1$ and $R^2$ are attached forms a heterocyclic ring, and wherein the compound (I) is optionally in the form of an acid salt derived from an organic or inorganic acid;

with a nucleic acid; wherein a stable intercalated complex with DNA is formed with said compound.

11. The method according to claim 10, further comprising detecting said compound in a biological assay.

12. The method according to claim 10, further comprising detecting said compound in cytometry.

13. The method according to claim 12, wherein said compound is an N-oxide derivative.

14. The method according to claim 12, further comprising detecting said compound with a single beam or multibeam laser.

15. The method according to claim 10, further comprising detecting said compound in a microscope.

16. The method according to claim 15, wherein said compound is an N-oxide derivative.

17. The method according to claim 15, wherein said microscope is a confocal laser scanning microscope.

* * * * *